United States Patent [19]
Maxwell et al.

[11] Patent Number: 5,585,254
[45] Date of Patent: Dec. 17, 1996

[54] AUTONOMOUS PARVOVIRUS GENE DELIVERY VEHICLES AND EXPRESSION VECTORS

[75] Inventors: Ian H. Maxwell, Denver; Jonathan Carlson; Joseph A. Corsini, both of Ft. Collins; Françoise Maxwell, Denver, all of Colo.; Solon L. Rhode, Omaha, Nebr.

[73] Assignee: University of Colorado Foundation, Inc., Boulder, Colo.

[21] Appl. No.: 42,419

[22] Filed: Apr. 2, 1993

Related U.S. Application Data

[63] Continuation-in-part of Ser. No. 685,628, Apr. 15, 1991, abandoned, which is a continuation-in-part of Ser. No. 88,086, Aug. 21, 1987, abandoned.

[51] Int. Cl.$^6$ .......................... C12N 15/63; C12N 15/86; C12N 7/01; C12N 15/64
[52] U.S. Cl. .................... 435/172.3; 435/320.1; 435/69.1; 435/70.3; 435/91.1; 435/91.21; 435/91.3; 435/91.31; 435/91.32; 435/235.1; 424/93.2; 424/405; 536/23.1; 536/23.7; 536/24.1; 536/24.5
[58] Field of Search .............................. 435/69.1, 69.8, 435/70.3, 172.3, 320.1, 235.1, 91.1, 91.21, 91.3, 91.31, 91.32; 935/32, 34, 57; 514/44; 424/417, 420, 450, 405, 93.2; 536/23.1, 23.7, 24.5, 24.1

[56] References Cited

U.S. PATENT DOCUMENTS

| | | | |
|---|---|---|---|
| 4,396,601 | 8/1983 | Salser et al. | 424/94 |
| 4,419,446 | 12/1983 | Howley et al. | 435/68 |
| 4,497,796 | 2/1985 | Salser et al. | 424/95 |
| 4,686,186 | 8/1987 | Sugden | 435/243 |
| 4,797,368 | 1/1989 | Carter et al. | 435/320 |
| 4,828,987 | 5/1989 | Kopchick et al. | 435/68 |
| 5,032,407 | 7/1991 | Wagner et al. | 424/520 |
| 5,087,617 | 2/1992 | Smith et al. | 514/44 |

FOREIGN PATENT DOCUMENTS

| | | |
|---|---|---|
| WO90/07936 | 7/1990 | WIPO. |
| WO91/06309 | 5/1991 | WIPO. |
| WO91/18088 | 11/1991 | WIPO. |

OTHER PUBLICATIONS

S. Cotmore et al. Adv. in Virus Res., vol. 33 (87) pp. 91–174.
J. Sambrook et al., "Molecular Cloning, 2nd Ed", C S Harbor, NY, CSH Lab Press, 1989, pp. 16.30–16.32, 16.39–16.41, 16.45–16.47, 16.50–16.51, 16.54–16.55, 16.73–16.81.
S. J. Russell et al. J. Virology, vol. 66, No. 5, (May '92) pp. 2821–2828.
Siegl, G., et al. FEMS Microbiology Reviews, vol. 46 (1987) pp. 433–450.
O. Shohat et al. Oncogene, vol. 1, (1987) pp. 277–283.
G. Wu et al. J. Biol. Chem., vol. 266 (1991) pp. 14338–14342.
C. Nicolau et al., P.N.A.S., vol. 80 (1983) pp. 1068–1072.
N. Dillon Tibtech, vol. 11 (May '93) pp. 167–173.
U. Strahle et al. PNAS, vol. 84 (Nov. '87) pp. 7871–7875.
D. LaFace et al. Virology, vol. 162 ('88) pp. 483–486.
"Gene Therapy: New Protocols, New Vectors, No Germ Line", pp. 597–599, 1992, ASM News, vol. 58, No. 11.
Ball–Goodrich et. al., "Two Amino Acid Substitutions within the Capsid are Coordinately Required for Acquisition of Fibrotropism by the Lymphotropic Strain of Minute Virus of Mice", pp. 3415–3423, 1992, J. Virol., vol. 66, No. 6, (Jun).
Beutler et. al., "Gene Transfer in the Treatment of Hematologic Disease", pp. 857–860, 1990, Exp. Hematol., vol. 18.
Breitman et. al., "Genetic Ablation: Targeted Expression of A Toxin Gene Causes Microphthalmia in Transgenic Mice", pp. 1563–1565, 1987, Science, vol. 238, (Dec.).
Breitman et. al., "Genetic Ablation in Transgenic Mice with an Attenuated Diphtheria Toxin A Gene", pp. 474–479, 1990, Mol. Cell. Biol., vol. 10, No. 2, (Feb.).
Clemens et. al., "Regulated Expression of the Feline Panleukopenia Virus P38 Promoter on Extrachromosomal FPV/EBV Chimeric Plasmids", pp. 2737–2745, 1989, J. Virol., vol. 63, No. 6, (Jun.).
Clemens et. al., "Cloning of Minute Virus of Mice cDNAs and Preliminary Analysis of Individual Viral Proteins Expressed in Murine Cells", pp. 3967–3973, 1990, J. Virol., vol. 64, No. 8, (Aug.).
de Wet et. al., "Firefly Luciferase Gene: Structure and Expression in Mammalian Cells", pp. 725–737, 1987, Mol. Cell. Biol., vol. 7, No. 2, (Feb.).
Diffoot et. al., "Identical Ends are not Required for the Equal Encapsidation of Plus—and Minus–Strand Parvovirus LuIII DNA", pp. 3180–3184, 1989, J. Virol., vol. 63, No. 7, (Jul.).
Diffoot et. al., "The Complete Nucleotide Sequence of Parvovirus LuIII and Localization of a Unique Sequence Possibly Responsible for Its Encapsidation Pattern", pp. 339–345, 1993, Virol., vol. 192.
Dixit et. al., "Construction and Expression of a Recombinant Adeno–Associated Virus that Harbors a Human β–Globin–Encoding cDNA", pp. 253–257, 1991, Gene, vol. 104.

(List continued on next page.)

*Primary Examiner*—Charles C. P. Rories
*Attorney, Agent, or Firm*—Sheridan Ross & McIntosh

[57] ABSTRACT

The present invention relates to novel recombinant autonomous parvovirus vectors, novel recombinant virus particles, and novel gene delivery vehicles that can be used to selectively target heterologous nucleic acid sequences to desired cell types and to selectively express such sequences in such desired cell types. Recombinant autonomous parvovirus gene delivery vehicles are particularly advantageous for transient gene therapy, and are especially well-suited to treat diseases in which there is rapid cell growth, such as cancer. Also included is the use of recombinant vectors of the present invention to produce RNA and protein products in cell culture.

83 Claims, 4 Drawing Sheets

OTHER PUBLICATIONS

Ellis et. al., "Replacement of Insulin Receptor Tyrosine Residues 1162 and 1163 Compromises Insulin–Stimulated Kinase Activity and Uptake of 2–Deoxyglucose", pp. 721–732, 1986, Cell, vol. 45, (Jun.).

Flotte et. al., "Gene Expression from Adeno–associated Virus Vectors in Airway Epithelial Cells", pp. 349–356, 1992, AM. J. Respir. Cell Mol. Biol., vol. 7.

Gossen et al., "Tight Control of Gene Expression in Mammalian Cells by Tetracycline–Responsive Promoters", pp. 5547–5551, 1992, Proc. Natl. Acad. Sci. USA, vol. 89.

Gould–Fogerite et. al., "Chimerasome–Mediated Gene Transfer in vitro and in vivo", pp. 429–438, 1989, Gene, vol. 84.

Hanson et. al., "Parvovirus NS1 Stimulates P4 Expression by Interaction with the Terminal Repeats and through DNA Amplification", pp. 4325–4333, 1991, J. Virol., vol. 65, No. 8, (Aug.).

Harrison et al., "Activation of a Diphtheria Toxin A Gene by Expression of Human Immunodeficiency Virus–1 Tat and Rev Proteins in Transfected Cells", pp. 53–60, 1991, Hum. Gene Therapy, vol. 2.

Hirt, "Selective Extraction of Polyoma DNA from Infected Mouse Cell Cultures", pp. 365–369, 1967, J. Mol. Biol., vol. 26.

Kajigaya et. al., "Self–Assembled 819 Parvovirus Capsids, Produced in a Baculovirus System, are Antigenically and Immunogenically Similar to Native Virions", pp. 4646–4650, 1991, Proc. Natl. Acad. Sci. USA, vol. 88, (Jun.).

LaFace et. al. "Gene Transfer into Hematopoietic Progenitor Cells Mediated by an Adeno–Associated Virus Vector", pp. 483–486, 1988, Virology, vol. 162.

Lieberman et. al., "The Constitution of a Progesterone Response Element", pp. 515–527, 1993, Mol. Endo., vol. 7, No. 4.

Liu et. al., "Indiscriminate Activity from the B19 Parvovirus P6 Promoter in Nonpermissive Cells", pp. 361–364, 1991, Virology, vol. 182.

Maxwell et. al., "Cloning Sequence Determination, and Expression in Transfected Cells of the Coding Sequence for the tox 176 Attenuated Diphtheria Toxin A Chain", pp. 1576–1579, 1987, Mol. Cell. Biol., vol. 7, No. 4, (Apr.).

Maxwell et. al., "Electroporation of Mammalian Cells with a Firefly Luciferase Expression Plasmid: Kinetics of Transient Expression Differ Markedly Among Cell Types", pp. 557–562, 1988, DNA, vol. 7, No. 8.

Maxwell et. al., "Expression of the Diphtheria Toxin A–Chain Coding Sequence under the Control of Promoters and Enhancers from Immunoglobulin Genes as a Means of Directing Toxicity to B–Lymphoid Cells", pp. 4299–4304, 1991, Cancer Research, vol. 51, (Aug.).

Maxwell et. al., "Regulated Expression of a Diphtheria Toxin A–Chain Gene Transfected into Human Cells: Possible Strategy for Inducing Cancer Cell Suicide", pp. 4660–4664, 1986, Cancer Research, vol. 46, (Sep.).

Muro–Cacho et al., "Gene Transfer in Human Lymphocytes Using a Vector Based on Adeno–Associated Virus", pp. 231–237, 1992, J. Immunotherapy, vol. 11, No. 4.

Muzyczka, "Use of Adeno–Associated Virus as a General Transduction Vector for Mammalian Cells", pp. 97–129, 1992, Curr. Top. Microbiol. Immunol., vol. 158.

Ohi et. al., "Construction and Replication of an Adeno–Associated Virus Expression Vector that Contains Human β–Globin cDNA", pp. 279–282, 1990, Gene, vol. 89.

Palmiter et. el., "Cell Lineage Ablation in Transgenic Mice by Cell–Specific Expression of a Toxin Gene", pp. 435–443, 1987, Cell, vol. 50, (Jul.).

Reitz et. al., "The p39 Promoter of Minute Virus of Mice Directs High Levels of Bovine Growth Hormone Gene Expression in the Bovine Papilloma Virus Shuttle Vector", pp. 297–300, 1987, Gene, vol. 56.

Rhode III, "Trans–Activation of Parvovirus $P_{38}$ Promoter by the 76K Noncapsid Protein", pp. 886–889, 1985, J. Virol., vol. 55, No. 3, (Sep.).

Rhode III, "Both Excision and Replication of Cloned Autonomous Parvovirus DNA Require the NS1 (rep) Protein", pp. 4249–4256, 1989, J. Virol., vol. 63, No. 10, (Oct.).

Rosenfeld et. al., "Adenovirus–Mediated Transfer of a Recombinant αl–Antitrypsin Gene to the Lung Epithelium in Vivo", pp. 431–434, 1991, Science, vol. 252, (Apr.).

Samulski et. al., "Helper–Free Stocks of Recombinant Adeno–Associated Viruses: Normal Integration Does Not Require Viral Gene Expression", pp. 3822–3828, 1989, J. Virol, vol. 63, No. 9, (Sep.).

Sinkovics, "Oncogenes–Antioncogens and Virus Therapy of Cancer", pp. 1281–1290, 1989, Anticancancer Res., vol. 9.

Srivastava et. al., "construction of a Recombinant Human Parvovirus B19: Adano–Associated Virus 2 (AAV) DNA Inverted Terminal Repeats are Functional in an AAV–B19 Hybrid Virus", pp. 8078–8082, 1989, Proc. Natl. Acad. Sci. USA, vol. 86, (Oct.).

Stratford–Perricaudet et al., "Evaluation of the Transfer and Expression in Mice of an Enzyme–Encoding Gene Using a Human Adenovirus Vector", pp. 241–256, 1990, Hum. Gene Therapy, vol. 1.

Tani et al., "Implantation of Fibroblasts Transfected with Human Granulocyte Colony–Stimulating Factor cDNA into Mice as a Model of Cytokine–Supplement Gene Therapy", pp. 1274–1280, 1989, Blood, vol. 74, No. 4, (Sep.).

Tattersall et. al. al., "Reciprocal Productive and Restrictive Virus–Cell Interaction of Immunosuppressive and Prototype Strains of Minute Virus of Mice", pp. 944–955, 1983, J. Virol., vol. 46, No. 3, (Jun.).

Tratschin et. al., "A Human Parvovirus, Adeno–Associated Virus, as a Eucaryotic Vector: Transient Expression and Encapsidation of the Procaryotic Gene for Chloramphenicol Acetyltransferase", pp. 2072–2081, 1984, Mol. Cell. Biol., vol. 4, No. 10, (Oct.).

AUTONOMOUS PARVOVIRUS GENE DELIVERY VEHICLES AND EXPRESSION VECTORS

This invention was made with government support under Grant No. CA 50285 awarded by the National Cancer Institute, National Institutes of Health. The government has certain rights to this invention.

CROSS-REFERENCE TO RELATED APPLICATIONS

The present application is a continuation-in-part of U.S. patent application Ser. No. 07/685,628, entitled "Cell Suicide Mediated by Cell-Selective Expression of Toxin Genes", filed Apr. 15, 1991, now abandoned, which is a continuation-in-part of U.S. patent application Ser. No. 07/088,086, entitled "Cell Suicide Mediated by Cell-Selective Expression of Toxin Genes", filed Aug. 21, 1987, now abandoned, both of which are incorporated by reference herein in their entirety.

FIELD OF THE INVENTION

The present invention relates to novel gene delivery vehicles, and particularly to the use of autonomous parvovirus vectors to transfer genes to and express genes in selective cell types.

BACKGROUND OF THE INVENTION

Only recently has it been possible to transfer heterologous (i.e., foreign) nucleic acid sequences, such as control elements or gene coding regions, into cells, let alone into animals. Investigators have been testing a variety of delivery vehicles to both introduce and maintain a gene in the cells of an animal, such as a human, to correct, for example, inborn errors of metabolism.

The majority of gene transfer vehicles tested have included virus vectors that integrate into the host genome. Although integration of a vector may be desirable to achieve stable gene transfer, there is a danger that the vector may integrate at a position that could harm the animal. For example, one concern about the use of retroviruses and adeno-associated viruses is that, since integration of the virus vector typically cannot be controlled, there is a potential danger that, upon integration, the vector will activate the expression of an undesired gene located near it, such as an oncogene.

Most research and clinical efforts to date have used retroviruses as drug delivery vehicles, particularly to deliver genes to hematopoietic cells; see, for example, Beutler et al., pp. 857–860, 1990, Exp. Hematol., Vol. 18; Kopchick et al., U.S. Pat. No. 4,828,987, issued May 9, 1989; Wagner et al., U.S. Pat. No. 5,032,407, issued Jul. 16, 1991; Goldsmith et al., PCT International Publication No. WO 90/07936. However, in many cases, expression of recombinant retrovirus vectors in undifferentiated cells has been suppressed; see, for example, Beutler, ibid. In addition, retroviruses are quite labile, grow to relatively low titers (particularly recombinant retroviruses), are difficult to handle without significant infectivity loss, and exhibit a limited host range.

Adeno-associated viruses are also being evaluated as possible gene delivery vehicles. For a review, see Muzyczka, pp. 97–129, 1992, Current Topics in Microbiology and Immunology, Vol. 158; also see, for example Carter et al., U.S. Pat. No. 4,797,368, issued Jan. 10, 1989; Chatterjee et al., PCT International Publication No. WO 91/18088. Adeno-associated viruses are a genus of parvoviruses that integrate into the host genome and require either adenovirus or a herpes virus to replicate. Little is known about the long-term effects of these viruses on a host, such as the effects of integration. In addition, due to their dependence on other viruses to replicate, adeno-associated viruses are difficult to produce.

Researchers are also assessing the usefulness of viruses that remain essentially autonomous (i.e., do not appear to integrate to a significant amount) to effect stable gene transfer. Examples of such viruses include adenovirus, bovine papilloma virus, and various herpes viruses. See, for example, Rosenfeld et al., pp. 431–434, 1991, Science, Vol 252; Stratford-Perricaudet et al., pp. 241–256, 1990, Human Gene Therapy, Vol. 1; Tani et al., pp. 1274–1280, 1989, Blood, Vol. 74; Beutler et al., ibid.; Howley et al., U.S. Pat. No. 4,419,446, issued Dec. 6, 1983; Salser et al., U.S. Pat. No. 4,497,796, issued Feb. 5, 1985. There are, however, a variety of safety concerns about a number of such viruses, and the host range of at least some of these viruses is limited. In addition, production of such viruses is complicated by the number of virus proteins required for virus vector amplification and, if desired, encapsidation. There is also a concern that replication-defective vectors may recombine with helper virus vectors to create infectious viruses.

Additional methods to deliver genes, including direct administration of naked DNA or RNA molecules and attachment of nucleic acids to carriers, such as liposomes, are being developed. See, for example, Gould-Fogerite et al., pp. 429–438, 1989 Gene, Vol. 84; Brigham, PCT International Publication No. WO 91/06309.

Despite the progress made to date, there is still a need for gene delivery vehicles that target appropriate cell types when administered in vivo (i.e., directly administered to the animal rather than transferring genes to cells outside the body) and that elicit gene expression in desired cell types. There is also a need for a gene delivery vehicle that effects transient gene therapy, particularly in the treatment of a number of diseases, such as cancer and diseases caused by infectious agents. For these diseases, it may be desirable to target a gene encoding a cytotoxin to affected cells.

Certain toxin-encoding genes, such as the gene for diphtheria toxin, have been shown to be selectively expressed in certain desired cell types, but in general, such targeting has been achieved by operatively linking the gene to a transcription control element that is substantially only activated in the desired cell type. See, for example, Maxwell et al., pp. 4660–4664, 1986, Cancer Res., Vol. 46; Maxwell et al., pp. 4299–4304, 1991, Cancer Res., Vol. 51; Palmiter et al., pp. 435–443, 1987, Cell, Vol. 50; Breitman et al., pp. 1563–1565, 1987, Science, Vol. 238; Breitman et al., pp. 474–479, 1990, Mol. Cell. Biol., Vol. 10; Harrison et al., pp. 53–60, 1991, Human Gene Therapy, Vol. 2. Such selective expression of genes transferred to a cell by a vector has been tested in cell culture and transgenic animals. There still remains, however, a need to develop vehicles that selectively deliver such vectors to desired cell types, particularly for human applications. There is also a need to develop gene delivery vehicles that are easier to produce than vehicles based on, for example, adeno-associated viruses, adenoviruses, or retroviruses.

Autonomous parvoviruses are small DNA viruses that replicate autonomously in rapidly dividing cells. The genomes of autonomous parvoviruses apparently do not integrate, at least not at a detectable level. Autonomous parvovirus genomes are single-stranded DNA molecules about 5 kilobases (kb) in size. The genomes are organized such that the NS gene encoding the nonstructural polypeptides NS1 and NS2 is located on the left side of the genome and the VP gene encoding the structural polypeptides required for capsid formation are on the right side of the genome. Expression of the nonstructural polypeptides is controlled by a transcription control sequence called P4 in most parvoviruses, which is located at about map unit position 4 of the genome (assuming the entire genome is 100 map units and numbering is from left to right). Expression of the structural polypeptides is controlled by a transcription control sequence called P38, P39 or P40 in most parvoviruses, which is located at about map unit position 38 to about 40, depending on the autonomous parvovirus. NS1 serves as a trans-activator of the latter transcription control sequence. NS1 is also essential for virus replication and appears to be the primary mediator of parvovirus cytotoxicity, particularly against tumor cells. Autonomous parvovirus genomes also have inverted repeat sequences (i.e., palindromes) at each end which contain essential signals for replication and encapsidation of the virus. There have been several studies on the mechanistics of autonomous parvovirus replication, gene expression, encapsidation, and cytotoxicity. See, for example, Sinkovics, pp. 1281–1290, 1989, *Anticancer Res.*, Vol 9. To the inventors' knowledge, however, autonomous parvoviruses have not been used as gene delivery vehicles prior to the present invention.

SUMMARY OF THE INVENTION

The present invention relates to novel recombinant autonomous parvovirus vectors, novel recombinant virus particles, and novel gene delivery vehicles that can be used to selectively target heterologous nucleic acid sequences to desired cell types and to selectively express such sequences in such desired cell types. Recombinant autonomous parvovirus gene delivery vehicles are particularly advantageous for transient gene therapy, and are especially well-suited to treat diseases in which there is rapid cell growth, such as cancer, due to autonomous parvoviruses' tropism for rapidly dividing cells.

One embodiment of the present invention is a recombinant vector that includes an autonomous parvovirus nucleic acid sequence, or functional equivalent thereof, joined to at least one heterologous nucleic acid sequence, the vector being capable of transferring the heterologous nucleic acid sequence to a host cell. Preferred heterologous nucleic acid sequences include heterologous control elements, heterologous coding regions, and/or heterologous control elements operatively linked to heterologous coding regions.

Expression of autonomous parvovirus and/or heterologous coding regions contained in the recombinant vectors is preferably regulated by a response element that permits the selective expression of the coding region in a desired cell type and/or in response to the presence of certain compounds. Preferred response elements include cell-selective response elements and hormone receptor response elements. In one embodiment, the recombinant vector is capable of effecting transient (i.e., temporal, not permanent) expression of the heterologous nucleic acid sequence in a host cell.

Preferred parvovirus nucleic acid sequences contained in recombinant vectors of the present invention include LuIII parvovirus, minute virus of mice, hamster parvovirus, feline panleukopenia virus, canine parvovirus, porcine parvovirus, latent rat virus, mink enteritis virus, human parvovirus, bovine parvovirus, and Aleutian mink disease parvovirus nucleic acid sequences, with LuIII parvovirus nucleic acid sequences being particularly preferred. A particularly preferred recombinant vector includes the left and right terminal repeat sequences of an autonomous parvovirus genome but is essentially devoid of nucleic acid sequences encoding either structural or nonstructural autonomous parvovirus polypeptides, the autonomous parvovirus nucleic acid sequence being joined to at least one heterologous nucleic acid sequence, the expression of which is regulated by a control element.

Preferred coding regions of the present invention include, but are not limited to, nucleic acid sequences that encode protein or RNA products such as cytotoxic agents, immunopotentiating agents, vaccine antigens, antisense RNA molecules, ribozymes, RNA-based drugs, and functional equivalents thereof.

A particularly preferred recombinant vector of the present invention includes an autonomous parvovirus nucleic acid sequence joined to a heterologous nucleic acid sequence that comprises a cancer cell-selective response element operatively joined to a promoter and a coding region encoding for a cytotoxic agent. Introduction (i.e., transfer) of such a vector into a host cancer cell essentially inhibits cancer cell growth.

Another embodiment of the present invention is a recombinant virus particle that includes a recombinant vector of the present invention packaged in a virus capsid, the virus capsid preferably being an autonomous parvovirus capsid. According to the present invention, the recombinant vector can be pseudotyped by packaging the vector in a capsid of a virus species other than the species of the parvovirus nucleic acid sequence.

Yet another embodiment of the present invention is a recombinant virus particle having certain characteristics of an autonomous parvovirus particle, including high stability, essential lack of integration, high titer, and maintenance of infectivity upon concentration.

The present invention also includes a gene delivery vehicle comprising a recombinant vector of the present invention. The recombinant vector can be encapsidated in a virus particle or attached to a carrier, such as a liposome or virus. Preferably the virus particle or carrier is capable of targeting the recombinant vector to a selected population of host cells, such as cancer cells or cells infected by an infectious agent.

Another embodiment of the present invention is a method for transferring a heterologous nucleic acid sequence into a host cell that includes introducing into the cell a recombinant vector of the present invention, which preferably is either encapsidated into a recombinant viral particle or attached to a carrier effective to deliver the vehicle to the cell.

Yet another embodiment of the present invention is a method for effecting transient gene therapy in an animal that includes administering to the animal a recombinant vector of the present invention and effecting expression of the heterologous nucleic acid sequence in at least a selected population of cells in the animal.

The present invention also includes a method for treating an animal ex vivo comprising removing a selected population of host cells from the animal; infecting that cell population with a recombinant virus particle of the present invention; and reintroducing the infected cells into the animal.

A preferred embodiment of the present invention is a method for substantially destroying a selected population of cells in an animal which includes administering to the animal at least one recombinant vector of the present invention that contains at least one heterologous response element that is selectively expressed by the cell population. The response element is operatively linked to a promoter and to a coding region capable of encoding a compound that is substantially cytotoxic to the cell population. Preferred compounds include antisense RNA molecules, ribozymes, RNA-based drugs, and cytotoxic proteins. Preferred cell populations include cancer cells and cells infected with an infectious agent.

Another embodiment of the present invention is a method to produce a recombinant virus particle useful in the delivery of a gene to a targeted cell that includes co-transfecting a host cell with a recombinant vector of the present invention and with a helper construct capable of effecting vector amplification and/or packaging; and culturing the transfected host cell in an effective medium to produce a recombinant virus particle.

The present invention also includes the use of recombinant vectors of the present invention to produce RNA and protein products. In one embodiment, a method to produce a heterologous protein or RNA product includes transfecting a host cell with a recombinant vector having an autonomous parvovirus nucleic acid sequence joined to at least one heterologous nucleic acid sequence encoding the product; and culturing the transfected cell in an effective medium to produce the product. If desired, the host cell can also be transfected with a helper construct capable of effecting replication of the vector.

Also included in the present invention are recombinant vectors pGLuLUC, pGLuLUCΔSV, pGLuZ, pTOLuLUC, pTO-Lu, pTO-LuΔVP, pPRE-Lu, pMMTV-Lu, and pPRE-LuDT-A; recombinant virus particles LuIII:pGLuLUCΔSV, LuIII:pGLuZ, LuIII:pTOLuLUC, LuIII:pPRELuDT-A, LuIII:pTO-Lu, LuIII:pTO-LuΔVP, LuIII:pPRE-Lu, LuIII:pMMTV-Lu, Hi:pGLuLUCΔSV, MVMi:pGLuLUCΔSV, and MVMp:pGLuLUCΔSV; and helper constructs pSVLu, pMVMpΔ, and pMVMi-6.

DETAILED DESCRIPTION OF THE INVENTION

Figure 1:
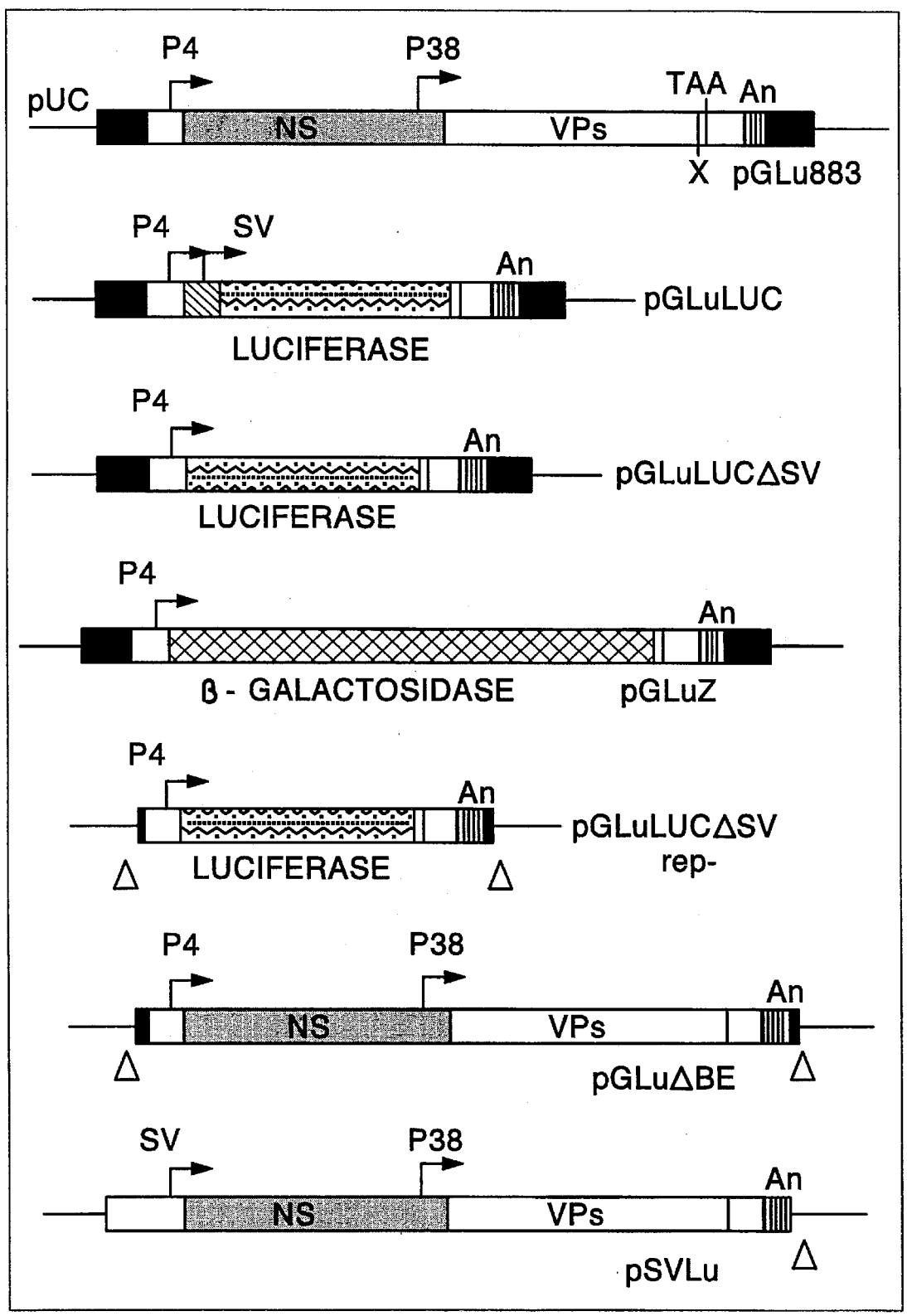
FIG. 1 includes schematic drawings depicting portions of several recombinant autonomous parvovirus vectors and helper constructs of the present invention.

The present invention relates to novel recombinant autonomous parvovirus vectors, recombinant virus particles containing such vectors, recombinant virus particles that are functionally equivalent to autonomous parvovirus particles, and methods to produce and use such vectors and virus particles. Vectors and virus particles of the present invention are advantageous because they can be used to both selectively deliver genes to desired cell types and to selectively express genes in desired cell types. Such vectors and virus particles can also be used to produce proteins and RNA products in, for example, cell culture or transgenic animals.

The present invention is particularly advantageous because it allows gene therapy to be selectively controlled at two levels: (a) a nucleic acid sequence can be selectively targeted to certain cell types by choosing an appropriate virus capsid or other carrier that is capable of delivering a recombinant vector containing the nucleic acid sequence to the selected cell types; and (b) a nucleic acid sequence can be selectively expressed in certain cell types by activating an appropriate control element operatively linked to the nucleic acid sequence.

One embodiment of the present invention is a composition that is capable of delivering a heterologous (i.e., foreign) nucleic acid sequence to a host cell. The composition includes at least one virus particle comprising a vector having a virus nucleic acid sequence containing at least one heterologous nucleic acid sequence. Preferably, the vector is packaged within a virus capsid, such as a virus coat or envelope, to form a recombinant virus particle. Preferred recombinant virus particles of the present invention are recombinant autonomous parvovirus particles.

Autonomous parvoviruses are small animal viruses that are able to infect a variety of cell types, from insect to human. Autonomous parvoviruses are preferred over several gene delivery vehicles currently in use, such as adenoviruses, retroviruses, and adeno-associated viruses for a number of reasons. Autonomous parvoviruses are remarkably stable, being significantly more stable in the presence of heat and organic solvents. For example, whereas autonomous parvoviruses survive at 60° C. for several hours, adenoviruses are killed within about 30 minutes and retroviruses in an even shorter period of time under similar conditions. Autonomous parvoviruses also grow to high titers (up to about $1 \times 10^9$ infectious units per milliliter [ml]), whereas although wild-type retrovirus titers of about $10^7$ infectious units per ml can be achieved, recombinant retrovirus titers are usually only about $10^4$ infectious units per ml. In addition, autonomous parvoviruses, unlike retroviruses, can be concentrated with substantially no loss of infectivity. The ability to concentrate recombinant autonomous parvoviruses is particularly important since production of recombinant autonomous parvovirus particles often leads to production titers significantly less than about $10^9$ infectious units per ml, and it is desirable to deliver the particles at a concentration of about $10^9$ infectious units per ml. In contrast, retroviruses cannot be produced at such high titers because concentration can result in substantial loss of infectivity.

Due to the small size of autonomous parvoviruses compared to, for example, adenoviruses, which have double-stranded genomes of about 35 kilobase pairs, it is at least theoretically possible to produce more autonomous parvoviruses than adenoviruses per unit substrate. In addition, to date, only about 20 percent of the adenovirus genome has been replaced by heterologous nucleic acid sequences. In contrast, the present inventors have unexpectedly found that at least about 90 percent of the autonomous parvovirus genome can be replaced by heterologous nucleic acid sequences.

Autonomous parvoviruses are able to replicate without a helper virus. Adeno-associated viruses, in contrast, require either an adenovirus or herpes virus to replicate. Furthermore, autonomous parvoviruses, unlike retroviruses and adeno-associated viruses, apparently do not integrate to any significant degree, making autonomous parvoviruses a virus particle of choice for transient gene therapy, and particularly for cancer therapy, as disclosed hereinafter in greater detail.

The inventors have discovered that such advantages of autonomous parvovirus make recombinant autonomous parvovirus particles especially well-suited as gene delivery vehicles, particularly to effect transient gene delivery. As used herein, the term "functionally equivalent recombinant autonomous parvovirus particle" refers to any recombinant virus particle that is similar to an autonomous parvovirus with respect to stability, essential lack of integration (i.e., as yet undetectable), high titer, and maintenance of infectivity upon concentration.

A recombinant vector of the present invention is a nucleic acid sequence comprising a virus nucleic acid sequence joined to (i.e., ligated to), or containing, at least one heterologous nucleic acid sequence, the vector being able to transfer (i.e., deliver or introduce) the heterologous nucleic acid sequence to a host cell. The recombinant vector can be either RNA or DNA and can be either single-stranded or double-stranded. Since it is technically difficult to perform recombinant techniques on RNA or on single-stranded DNA, recombinant vectors are usually produced as double-stranded DNA molecules (using, for example, double-stranded cDNA copies of autonomous parvovirus genomes or including the vectors in bacterial plasmids) which can be converted into RNA or single-stranded DNA copies using techniques known to those skilled in the art.

Preferred virus nucleic acid sequences of the present invention are autonomous parvovirus nucleic acid sequences or functional equivalents thereof. As used herein, a "functional equivalent of an autonomous parvovirus nucleic acid sequence" is a sequence that encodes for a substantially similar protein or that itself functions in a manner substantially similar to an autonomous parvovirus nucleic acid sequence.

A functionally equivalent nucleic acid sequence can be obtained using methods known to those skilled in the art. See, for example, Sambrook et al., *Molecular Cloning: A Laboratory Manual*, Cold Spring Harbor Labs Press, 1989, which is incorporated herein by reference in its entirety. A nucleic acid sequence of the present invention can be isolated from natural sources or can be synthesized chemically. Such a nucleic acid sequence can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences using a variety of screening techniques known to one skilled in the art. In one embodiment of the present invention, a functionally equivalent autonomous parvovirus nucleic acid sequence can be selected by the sequence's ability to transfer a heterologous nucleic acid sequence to a host cell in a manner similar to an autonomous parvovirus nucleic acid sequence.

Suitable autonomous parvovirus nucleic acid sequences of the present invention include, but are not limited to, LuIII parvovirus (LuIII), minute virus of mice (MVM; e.g., MVMi and MVMp), hamster parvovirus (e.g., H1), feline panleukopenia virus, canine parvovirus, porcine parvovirus, latent rat virus, mink enteritis virus, human parvovirus (e.g., B19), bovine parvovirus, and Aleutian mink disease parvovirus nucleic acid sequences. Preferred autonomous parvovirus nucleic acid sequences include LuIII, MVM, H1, feline panleukopenia virus, canine parvovirus, porcine parvovirus, latent rat virus, and mink enteritis virus nucleic acid sequences; with LuIII, MVM, H1, feline panleukopenia virus, and canine parvovirus nucleic acid sequences being more preferred; and with LuIII, MVMi, MVMp, and H1 nucleic acid sequences being even more preferred. A particularly preferred autonomous parvovirus nucleic acid sequence is a LuIII nucleic acid sequence. LuIII parvovirus is a parvovirus of unknown origin that was isolated as a contaminant of a substrain of human permanent cell line Lu106. The LuIII parvovirus exhibits high infectivity. pGLu883, a genomic clone of LuIII DNA (see Diffoot et al., pp. 3180–3184, 1989, *J. Virology*, Vol. 63; Diffoot et al., pp. 339–345, 1993, *Virology*, Vol. 192) is particularly stable and, as such, is a preferred starting material for producing recombinant vectors of the present invention.

To be packaged inside virus capsids, recombinant vectors of the present invention necessarily will have size limitations dependent upon the capsid utilized. For example, autonomous parvoviruses are capable of packaging a vector up to about 5.5 kb in length. The composition and configuration of recombinant vectors can vary substantially. For example, the heterologous nucleic acid sequence present in a recombinant vector of about 5 kb can comprise merely the nucleotide changes required to effect a desired functional change in, for example, a parvovirus promoter or coding sequence. Alternatively, up to about 90 percent of an autonomous parvovirus genome can be modified to produce a desired heterologous vector. If recombinant vectors are delivered by virus particles other than parvovirus particles, the size of the recombinant vector will necessarily be limited by the amount of nucleic acid the capsid to be utilized is able to package. If recombinant vectors are delivered by transfection or bound to a carrier, such as a virus or liposome, size limitation is not an issue.

Recombinant parvovirus vectors of the present invention preferably include at least a functional left end inverted terminal repeat and a functional right end inverted terminal repeat. As used herein, a functional inverted terminal repeat refers to a stretch of nucleotides that includes the cis-acting signals required for replication and packaging that are normally found in parvovirus terminal repeats. For recombinant LuIII parvovirus vectors, the minimal autonomous parvovirus nucleic acid sequence required appears to include the first about 120 to about 150 bases of the left end and the last about 210 to about 250 bases of the right end of the LuIII genome.

Recombinant vectors of the present invention can be designed (a) to be capable of self-amplification (i.e., designed to replicate without a helper construct by, for example, retaining a functional NS gene as well as the inverted repeats); (b) to be capable of self-packaging (i.e., designed so that encapsidation occurs without a helper construct by, for example, retaining a functional VP gene as well as the inverted repeats); or (c) to be capable of self-amplification and self-packaging.

In one embodiment of the present invention, helper constructs are used to effect amplification and/or encapsidation of recombinant vectors which themselves are essentially self-amplification incompetent and/or self-packaging incompetent (i.e., recombinant vectors that are essentially devoid of nucleic acid sequences encoding nonstructural and/or structural autonomous parvovirus nucleic acid sequences). When such helper constructs are used, the recombinant vector can comprise up to about 4.6 kb of heterologous nucleic acid sequences. Thus, a large percentage of a vector can comprise foreign nucleic acid sequences. For example, heterologous nucleic acid sequences can essentially replace the parvovirus sequence from about nucleotide 265 to about nucleotide 4530, or the parvovirus sequence from about nucleotide 145 to about nucleotide 4677, based on the nucleotide numbering system for the genome of LuIII parvovirus (Diffoot et al., 1989, ibid.; the complete nucleic acid sequence of pGLu883 is reported in Diffoot et al., 1993, ibid.).

Heterologous nucleic acid sequences that can be inserted between autonomous parvovirus sequences can include one or more heterologous control elements and/or one or more heterologous coding regions. While introns can be incorporated into recombinant vectors of the present invention, they apparently are not required. It is also within the scope of the present invention to replace a parvovirus transcription control sequence with a heterologous transcription control sequence in order to direct selective expression of desired sequences. For example, the parvovirus NS gene can be transcribed in selective cell types by activation of heterologous transcription control sequences.

As used herein, a "heterologous nucleic acid sequence" is a sequence that is foreign to the autonomous parvovirus nucleic acid sequence; i.e., a sequence that is not normally found in wild-type autonomous parvovirus nucleic acid sequences or functional equivalents thereof. As such, a heterologous nucleic acid sequence can be derived from a foreign source (either by isolation of the nucleic acid sequence or by chemical synthesis of a nucleic acid sequence corresponding to a sequence isolated from a foreign source). A heterologous nucleic acid sequence can also be a modified autonomous parvovirus nucleic acid sequence that is functionally dissimilar to the unmodified nucleic acid sequence. Adeno-associated virus nucleic acid sequences are also considered to be heterologous nucleic acid sequences.

One embodiment of the present invention comprises a heterologous NS1 nucleic acid sequence that encodes an NS1 protein with properties distinct from those of naturally-occurring NS1, such as increased oncolytic activity toward tumor cells or increased ability to activate a parvovirus P38 transcription control element. In another embodiment, the nucleic acid sequences encoding structural polypeptides of one parvovirus type are modified to encode the structural polypeptides of another parvovirus type, thereby yielding a pseudotyped recombinant virus particle. Yet another embodiment of the present invention involves the use of a modified P4 transcription control element that exhibits an enhanced or reduced ability to activate transcription of coding regions operatively linked to that element.

Heterologous nucleic acid sequences of the present invention include, but are not limited to, heterologous control elements and heterologous coding regions. Heterologous control elements include, but are not limited to, response elements, promoters, other transcription initiation signals, transcription elongation signals, transcription termination signals, polyadenylation sites, splice sites, introns, RNA stability sequences, translation control signals, replication signals, packaging signals, sequences encoding repressors, sequences encoding trans-activators, and combinations thereof. As used herein, a "promoter" is any cis-acting nucleic acid sequence from which an RNA polymerase is able to initiate transcription. As used herein, a "response element" is a cis-acting nucleic acid sequence with which a trans-activating or trans-repressing compound interacts to either stimulate or suppress transcription. As such, response elements include operators, enhancers, and attenuators, as well as other positive and negative regulatory sequences. A transcription control sequence includes sequences that control the initiation, elongation, and/or termination of gene expression. A preferred transcription control sequence is a response element joined to a promoter in a manner effective to activate and initiate transcription.

As used herein, a heterologous coding region is a nucleic acid sequence that is capable of encoding a functional protein or a functional RNA. Functional proteins of the present invention can be encoded by any parvovirus or heterologous coding region that encodes a naturally-occurring (i.e., native) protein or a coding region that encodes a functional equivalent of that protein. As used herein, a "functionally equivalent" protein is a protein that has substantially the same biological activity as the naturally-occurring protein. Coding regions that encode functionally equivalent proteins can have deletions, additions, inversions, and/or substitutions which, in spite of such modifications, encode functional proteins. Proteins encoded by coding regions of the present invention can be modified by post-translation mechanisms, including glycosylation, acetylation, phosphorylation, carboxyl-terminal amidation, and proteolytic cleavage.

Functional RNA molecules that can be encoded by heterologous coding regions of the present invention include RNA-based drugs, antisense RNA molecules, and ribozymes. As used herein, an "RNA-based drug" is any RNA molecule that is of sufficient size and/or structure to be able to interact with an intracellular, extracellular, or membrane-bound component in order to prevent, treat, cure, or ameliorate a disease otherwise caused by that component. As used herein an "antisense RNA" is any RNA that is capable of substantially preventing expression of a protein, preferably a detrimental protein. As such, a nucleic acid sequence encoding such an RNA can be of any size and structure that, when expressed, will yield an antisense RNA having the defined function.

According to the present invention, control elements and coding regions of parvovirus and foreign (i.e., heterologous) origin can be combined in a variety of ways that can be appreciated by one skilled in the art. As used herein, the term "operatively linked" means that a coding region is joined (i.e., ligated) to a control element in such a manner that the regulatory signals of the control element (e.g., response elements and promoters) direct the expression of the coding region, ultimately leading to the production of the encoded protein or RNA. In one embodiment, at least one heterologous control element (e.g., a transcription control sequence comprising at least one heterologous response element joined to a promoter) is operatively linked to at least one parvovirus and/or heterologous coding region. In another embodiment, at least one heterologous coding region can be operatively linked to at least one of the following transcription control sequences: (a) a parvovirus transcription control sequence that regulates the expression of parvovirus nonstructural polypeptide genes, (b) a parvovirus transcription control sequence that regulates the expression of parvovirus structural polypeptide genes, and (c) a heterologous transcription control sequence that includes at least one heterologous response element and a promoter of either parvovirus or heterologous origin. In yet another embodiment, a heterologous nucleic acid sequence of the present invention includes at least one heterologous control element operatively linked to at least one heterologous coding region. A preferred parvovirus control element is the P4 transcription control sequence, with a LuIII P4 transcription control sequence being particularly preferred.

Essentially any parvovirus or heterologous coding region can be used in accordance with the present invention. Preferred coding regions encode a useful product that can be produced in, for example cell culture or transgenic animals, or that can effect gene therapy in a host cell into which they are introduced. Coding regions capable of effecting gene therapy include, but are not limited to, nucleic acid sequences that encode proteins or RNA molecules that can restore the function of a defective gene in the host cell; that can protect the host cell from disease, infection, or other harm; that can treat a disease or infection in the host cell; or that can effectively destroy (e.g., be cytotoxic to) undesired cells, such as cancer cells or cells infected with, for example, a virus, bacterium, or parasite. Preferred coding regions include coding regions for cytotoxic agents to effectively destroy undesired cells, coding regions for immunopotentiators that stimulate an immune response, such as cytokines and lymphokines, and coding regions for foreign antigens that can be used as vaccines (i.e., vaccine antigens).

Suitable cytotoxic agents include any agent that can be encoded by a nucleic acid sequence and that causes cells to die when the cells are exposed to the agent. Such cytotoxic agents include diphtheria toxins, ricin toxins, modeccin toxins, abrin toxins, Pseudomonas exotoxins, shiga toxins, pokeweed antiviral proteins, α-amanitin, ribosome inhibiting proteins, parvovirus nonstructural proteins, and enzymes like HSV (herpes simplex virus) thymidine kinase capable of metabolizing separately added drugs like gancyclovir to generate toxic metabolites. Cytotoxic agents can include the entire toxin or a functional equivalent thereof. For example, genes that naturally encode an A and B chain may be modified to encode an A chain. Cytotoxic agents can also include ribozymes, RNA molecules that are capable of killing cells or antisense RNA molecules that are capable of inhibiting cancer or infectious agent growth by preventing, for example, oncogene expression or virus replication or spreading (i.e., further infection). Preferred cytotoxic agents include diphtheria toxins, ricins, parvovirus nonstructural proteins, HSV thymidine kinase in conjunction with gancyclovir, and functional equivalents thereof; with diphtheria A-chain toxins, parvovirus NS1 proteins, and functional equivalents thereof being even more preferred. Suitable cytotoxic agents also include modified agents that exhibit less toxic activity and that can be encoded by a modified nucleic acid sequence. Such agents are suitable for use in recombinant vectors that exhibit some "leakiness" of gene expression such that the toxin gene is also expressed to some extent in cells other than those which are targeted. A preferred modified cytotoxic agent is the attenuated diphtheria toxin tox 176 (Maxwell et al., pp. 1576–1579, 1987, *Mol. Cell. Biol.*, Vol. 7).

Preferred immunopotentiators include interleukins and functional equivalents thereof. Suitable vaccine antigens include any protein that is capable of eliciting an immune response.

Heterologous coding regions of the present invention can also include coding regions that encode marker proteins that permit detection and quantitation of the ability of a control element to regulate gene expression. Suitable marker proteins include, but are not limited to, luciferase, β-galactosidase, chloramphenicol acetyltransferase, and alkaline phosphatase.

One aspect of the present invention concerns the ability to selectively express a parvovirus or heterologous nucleic acid sequence in particular cell types. As used herein, "selective expression" of a nucleic acid sequence refers to the ability of the nucleic acid sequence to be expressed in a desired cell type and/or under desired conditions (e.g., upon induction) but not to be substantially expressed in undesired cell types and/or under undesired conditions. That is, the site and degree of expression of a particular nucleic acid sequence is regulated in a desired fashion. To effect selective expression of a coding region according to the present invention, the coding region is operatively linked to a control element that is capable of being activated in the desired cell type and/or under predetermined conditions but is effectively suppressed in undesired cell types and/or conditions. Preferred control elements to effect selective expression include transcription control elements, with response elements in combination with promoters being particularly preferred. Proper orientation and positioning are important in operatively linking response elements, promoters, and coding regions to effect selective gene expression. Techniques to operatively link such elements are well known to those skilled in the art and several embodiments are disclosed herein.

As heretofore disclosed, a response element is a cis-acting nucleic acid sequence that interacts with a trans-activating or trans-repressing compound (usually a protein or a protein complexed with another material) to respectively stimulate or suppress transcription. Examples of response elements include operators, enhancers, attenuators, and other positive or negative regulatory elements. Response elements of the present invention can be cell-selective response elements, hormone receptor response elements, antibiotic response elements, or carbohydrate response elements.

As used herein, a "cell-selective response element" is a response element that is capable of being activated by a trans-activating regulatory element that is selectively produced in the cell type(s) to which a vector of the present invention is targeted. Any response element that permits selective expression in a desired cell type can be used in the present invention, and a number of nucleic acid sequences having such characteristics are known to those skilled in the art. Suitable response elements for use in the present invention depend on the cell type in which selective expression is desired and, particularly on whether the cell type is producing the trans-activator (i.e., trans-activating regulatory element) necessary for inducing expression. For example, elastase I enhancers, gamma crystallin gene response elements, immunoglobulin heavy and/or light chain enhancers, liver enhancers such as α-1-antitrypsin and serum albumin enhancers, chorionic gonadotropin α-chain or β-chain enhancers, interleukin-2 (IL-2) enhancers, IL-2 receptor enhancers, and human immunodeficiency virus (HIV) response elements (e.g., the TAR site) can be used to selectively express coding regions in, respectively, pancreatic acinar cells, lens tissue, B cells, liver cells, and HIV-infected cells.

As used herein, a "hormone receptor response element" is a response element that can be activated when a hormone, or a functional equivalent thereof, interacts with a cellular receptor for that hormone, thereby triggering internalization of the hormone-receptor complex which then selectively interacts with the appropriate hormone receptor response element (either directly or indirectly), thereby activating expression of genes operatively linked to the element. Hormone receptor response elements are preferably used to selectively express nucleic acid sequences in cells having receptors for the given hormone. For example, in view of the fact that some breast cancer cells contain an unusually high concentration of progesterone receptors, selective expression of a coding region in such breast cancer cells may be achieved by operatively linking the coding region to a progesterone receptor response element.

As used herein, an "antibiotic response element" is a response element that is regulated by the presence or absence of antibiotics, such as a tetracycline response element (i.e., a tetracycline operator or analog thereof) that is responsive to tetracycline. Similarly, a "carbohydrate response element" is a response element that is regulated by the presence or absence of certain carbohydrates or analogs thereof, such as a lac response element (i.e, a lac operator or analog thereof).

Preferred response elements of the present invention include tetracycline response elements, GAL4 response elements, lac response elements, progesterone receptor response elements, glucocorticoid receptor response elements, immunoglobulin kappa light chain enhancers, immunoglobulin heavy chain enhancers, HIV response elements, α-1-antitrypsin enhancers, serum albumin enhancers, IL-2 enhancers, IL-2 receptor enhancers, and chorionic gonadotropin α-chain or β-chain enhancers. More preferred response elements include progesterone receptor response elements, glucocorticoid receptor response elements, immunoglobulin kappa light chain enhancers, immunoglobulin heavy chain enhancers, HIV response elements, and α-1-antitrypsin enhancers.

Preferred recombinant vectors of the present invention include recombinant autonomous parvovirus vectors, or functional equivalents thereof, that contain a cell-selective response element, hormone receptor response element, or antibiotic response element which is operatively joined to a promoter and to a coding region that encodes a cytotoxic agent or a marker protein. Preferred recombinant vectors for use in cancer therapy include recombinant autonomous parvovirus vectors, or functional equivalents thereof, that contain a response element that is selectively activated in cancer cells joined to a promoter and to a coding region that encodes a cytotoxic agent, such as diphtheria toxin or a parvovirus NS1 protein. Particularly preferred recombinant vectors of the present invention include pGLuLUCΔSV, pGLuZ, pTOLuLUC, pTO-Lu, pTO-LuΔVP, pPRE-Lu, pMMTV-Lu, and pPRELuDT-A. Production of each of these vectors is described in the Examples below. The following strains have been deposited with the American Type Culture Collection, 12301 Parklawn Drive, Rockville, Md.: *Escherichia coli* strain HB101, PSVlu, ATCC Designation No. 98022, *E. coli* strain SURE, PTOluLUC, ATCC Designation No. 98023, and *E. coli* strain SURE, pGLuLUCΔSV, ATCC Designation No. 98024.

Another embodiment of the present invention is the transfer, or delivery, of nucleic acid sequences contained in a recombinant vector to a selected population of host cells, which can be either in culture, in a tissue, in an organ, or in a whole animal. As used herein, a "selected population of cells" is one or more cell types in which it is desired to effect expression of nucleic acid sequences contained in a vector of the present invention. A variety of methods can be used to transfer the recombinant vector including transfection of the vector into a host cell, encapsidation of the vector into a virus particle which is then delivered to the host cell, and attachment of the vector to a carrier which is then delivered to the host cell.

Transfection of vectors into a host cell can be accomplished using any process by which nucleic acid sequences are inserted into a cell. Transfection techniques for introducing vectors into cells ex vivo include, but are not limited to, chemically mediated transformation (e.g., using calcium phosphate or DEAE dextran), electroporation, microinjection, lipofection, protoplast fusion, and receptor mediated endocytosis, with electroporation being preferred. Transfection techniques for introducing vectors into cells in vivo include injection of the vector, preferably at a location proximate to the selected cell population; lipofection; and particle bombardment (e.g., using tungsten microparticles containing the recombinant vectors).

A preferred method for delivering a recombinant vector of the present invention is to incorporate the vector into a virus particle which is then introduced into a cell culture or animal. As used herein, a "recombinant virus particle" includes a recombinant vector of the present invention packaged, or encapsidated, in a virus capsid, which is preferably an adeno-associated or autonomous parvovirus capsid and more preferably an autonomous parvovirus capsid, or a functional equivalent thereof. A recombinant virus particle encapsidated in a capsid that is "functionally equivalent to a parvovirus capsid" provides the advantages of autonomous parvovirus particles with respect to, for example, high stability, essential lack of integration, high titer, and maintenance of infectivity upon concentration.

The virus capsid can be selected to permit nucleic acid sequences within the vector to be targeted to selective cell populations. One advantage of the use of parvovirus capsids is the extensive host range of parvoviruses, which ranges from insect to human. Preferred autonomous parvovirus capsids with which to encapsidate recombinant vectors of the present invention include, but are not limited to, LuIII parvovirus, minute virus of mice (e.g., MVMi or MVMp), hamster parvovirus (e.g. H1), feline panleukopenia virus, canine parvovirus, porcine parvovirus, latent rat virus, mink enteritis virus, human parvovirus (e.g., B19), bovine parvovirus, and Aleutian mink disease parvovirus capsids. Preferred autonomous parvovirus capsids include LuIII, MVMi, MVMp, H1, feline panleukopenia virus, canine parvovirus, porcine parvovirus, latent rat virus, and mink enteritis virus capsids; with LuIII, MVMi, MVMp, H1, feline panleukopenia virus, and canine parvovirus capsids being more preferred; and with LuIII, MVMi, MVMp, and H1 capsids being even more preferred. A particularly preferred autonomous parvovirus capsid is a LuIII capsid.

The inventors have discovered surprisingly that recombinant parvovirus-based vectors of the present invention can be pseudotyped such that the recombinant vector is derived from a different virus than the capsid. That is, the vector is packaged in a capsid of a parvovirus species (or type) other than the species (or type) of the parvovirus nucleic acid sequence comprising the vector. The ability to pseudotype recombinant vectors of the present invention greatly extends the host range of the vectors and permits additional targeting strategies for gene transfer. The inventors have shown, for example, that recombinant vectors containing LuIII parvovirus nucleic acid sequences joined to a marker gene can be encapsidated in MVMi, MVMp, or H1 capsids, even though LuIII, MVM, and H1 exhibit different encapsidation patterns, with respect to the type of DNA strands packaged. Thus, a recombinant LuIII vector can be targeted to, for example, human astrocytes by encapsidating the vector in a LuIII capsid; to, for example, mouse T-lymphoblasts by encapsidating the vector in a MVMi capsid; to, for example, fibroblasts by encapsidating the vector in a MVMp capsid; and to, for example, rat gliosarcoma cells by encapsidating the vector in an H1 capsid. In another embodiment, a virus particle containing a feline leukopenia virus capsid, which is known to target feline hematopoietic cells, may be capable of targeting immunopotentiating and/or cytotoxic agents to cancerous and/or infected white blood cells.

Without being bound by theory, it is believed that adeno-associated viruses and autonomous parvoviruses are sufficiently similar that any recombinant autonomous parvovirus vector, or functional equivalent thereof, may be encapsidated in any adeno-associated virus or autonomous parvovirus capsid. Autonomous parvovirus capsids for pseudotyping include, but are not limited to, LuIII parvovirus, minute virus of mice (e.g., MVMi or MVMp), hamster parvovirus (e.g. Hi), feline panleukopenia virus, canine parvovirus, porcine parvovirus, latent rat virus, mink enteritis virus, human parvovirus (e.g., B19), bovine parvovirus, and Aleutian mink disease parvovirus capsids. Preferred autonomous parvovirus capsids include LuIII, MVMi, MVMp, H1, feline panleukopenia virus, canine parvovirus, porcine parvovirus, latent rat virus, and mink enteritis virus capsids; with LuIII, MVMi, MVMp, H1, feline panleukopenia virus, and canine parvovirus capsids being more preferred; and with LuIII, MVMi, MVMp, and H1 capsids being even more preferred. Particularly preferred pseudotyped virus particles include recombinant LuIII vectors encapsidated by MVMi, MVMp, or H1 capsids.

Preferred recombinant virus particles of the present invention include virus particles that contain a capsid capable of targeting a selected population of cells and that further contain recombinant autonomous parvovirus vectors, or functional equivalents thereof, having a cell-selective response element, hormone receptor response element, or antibiotic response element which is operatively joined to a promoter and to a coding region that encodes a cytotoxic agent or a marker protein. Preferred recombinant virus particles for use in cancer therapy include capsids targeted to cancer cells and recombinant autonomous parvovirus vectors, or functional equivalents thereof, that contain a response element that is selectively activated in cancer cells joined to a promoter and to a coding region that encodes a cytotoxic agent, such as diphtheria toxin or a parvovirus NS1 protein. Particularly preferred recombinant vectors to include in virus particles include pGLuLUCΔSV, pGLuZ, pTOLuLUC, pTO-Lu, pTO-LuΔVP, pPRE-Lu, pMMTV-Lu, and pPRELuDT-A. Particularly preferred recombinant virus particles include LuIII:pGLuLUCΔSV, LuIII:pGLuZ, LuIII:pTOLuLUC, LuIII:pPRELuDT-A, LuIII:pTO-Lu, LuIII:pTO-LuΔVP, LuIII:pPRE-Lu, LuIII:pMMTV-Lu, Hi:pGLuLUCΔSV, MVMi:pGLuLUCΔSV, and MVMp:pGLuLUCΔSV, in which the capsid type appears before and the recombinant vector type appears after the ":".

Moreover, it is within the scope of the invention that any virus capsid into which the vector can be encapsidated may be used to offer an even wider range of cell targeting possibilities. Suitable virus capsids include adenovirus, hepatitis virus, vaccinia virus, herpes virus, and other large DNA virus capsids. For example, an adenovirus capsid may be used to target a recombinant vector of the present invention to respiratory cells, and a hepatitis B virus capsid may be used to target a recombinant vector to liver cells. In such cases, the recombinant vector can approximate the size of the natural genome of such viruses.

Alternatively, a recombinant vector of the present invention can be attached to (e.g., adsorbed or chemically bound to) a carrier that is capable of transferring the vector to a host cell. Examples of carriers include, but are not limited to, viruses (e.g., "piggy-back" on the coat of an adenovirus), liposomes, and polymeric controlled release formulations. Such carriers can be modified to permit selective targeting of the vector using techniques known to those skilled in the art.

Vectors of the present invention can be attached to carriers using techniques known to those skilled in the art.

In accordance with the present invention, a recombinant virus particle can be produced by a method which at least in part depends upon whether the recombinant vector to be encapsidated contains sufficient genetic information to permit self-amplification and/or self-packaging (i.e., self-encapsidation). A virus particle containing a recombinant vector that is self-amplification and self-packaging competent can be produced by a method which includes the steps of: (a) transfecting a host cell with the recombinant vector; (b) culturing the transfected cell in an effective medium to produce a recombinant virus particle; and (c) recovering the particle. If, in contrast, the recombinant vector to be packaged into a virus particle is essentially self-amplification and/or self-packaging incompetent, host cells transfected with the vector must be supplemented with the necessary proteins to effect amplification and/or packaging. Such proteins can be supplied by, for example, co-transfecting the recombinant vector with at least one helper construct that contains nucleic acid sequences that encode the necessary nonstructural and/or structural proteins. Alternatively, the recombinant vector can be transfected into a host cell that already contains genes integrated into its chromosomal DNA and/or on extrachromosomal vectors that encode the nonstructural and/or structural polypeptides required to effect amplification and/or packaging of the recombinant vector (i.e., a host cell that is capable of packaging the recombinant vector into a virus particle). For example, a COS cell (an SV40-transformed monkey kidney cell) transformed with a parvovirus NS and/or VP gene can be used.

As used herein, a helper construct is a virus nucleic acid molecule that encodes the nonstructural and/or structural proteins required for amplification and/or packaging of the recombinant vector into a recombinant virus particle. The helper construct is preferably substantially unable to either effect self-packaging or to recombine with a recombinant vector to produce an infectious virus genome. Suitable helper constructs can be produced using the appropriate nonstructural and/or structural genes from any autonomous or adeno-associated parvovirus genome. The genes can be operatively linked to parvovirus and/or heterologous transcription control sequences. A preferable method to substantially inhibit self-packaging of the helper construct is to substantially remove cis-acting sequences in the terminal repeats of the genome that are required for packaging. Preferred helper constructs for the production of virus particles having LuIII capsids include pGLuΔBE and pSVLu. Details of the construction of such constructs are provided in the Examples below.

Helper constructs can also be produced which effect pseudotyping of recombinant vectors of the present invention. For example, a helper construct can contain an NS gene of one parvovirus type and a VP gene from a different parvovirus type. Examples of such helper constructs include pSR47B6 (which contains H1 NS and VP genes), pMVMpΔ (which contains MVMp NS and VP genes), and pMVMi-6 (which contains MVMi NS and VP genes). Details of the construction of such constructs are provided in the Examples below. Helper constructs can also encode capsids of other viruses, including, but not limited to, those of adenoviruses, hepatitis viruses, vaccinia viruses, herpes viruses, and other large DNA viruses capsids herpes viruses that can be used to pseudotype recombinant vectors of the present invention. Helper constructs can also encode parvovirus capsids into which targeting components of other virus capsids (i.e., the region(s) of the virus capsid that specify host range) can be integrated.

A number of host cells are suitable for recombinant virus particle production since parvoviruses have such wide host ranges. Suitable host cells include, but are not limited to, insect, avian, and mammalian cells, with mammalian cells being preferred. More preferred host cells include HeLa cells, adenovirus E1 region-transformed human fetal kidney cells (e.g., 293 cells), SV40-transformed human newborn kidney cells (e.g., NB324K cells), murine A9 fibroblast cells, murine iD5 hybrid cells, PEJ/Rat2 cells (Rat2 cells transformed by an activated H-ras oncogene), and COS cells.

As heretofore disclosed, transfection includes any means for introducing a nucleic acid sequence, such as a recombinant vector or a helper construct, into a host cell, including, but not limited to transformation, electroporation, microinjection, lipofection, adsorption, and protoplast fusion, with electroporation being preferred.

After transfection, transfected cells are cultured in an effective medium, using techniques such as those described in Rhode, pp. 4249–4256, 1989, *J. Virology*, Vol. 63. As used herein, an effective medium refers to any medium in which the transfected cells can be grown and in which they are able to produce recombinant virus particles. An effective medium is typically an aqueous medium comprising assimilable carbohydrate, nitrogen and phosphate sources, as well as appropriate salts, minerals, metals and other nutrients, such as vitamins and hormones. Culturing is carried out at a temperature, pH and oxygen content appropriate for the transfected cell. Such culturing conditions are well within the expertise of one of ordinary skill in the art. Examples of preferred effective media are included in the Examples below.

Recombinant virus particles can be recovered from the cultured transfected cells using a combination of standard techniques such as, but not limited to, ultracentrifugation, affinity chromatography, ion exchange chromatography, filtration, and hydrophobic interaction chromatography. A preferred recovery technique is ultrafiltration. Preferably, a recombinant virus particle of the present invention is recovered in "substantially pure" form. As used herein, "substantially pure" refers to a purity that allows for the effective use of the recombinant virus particle as a gene delivery vehicle without substantial negative side effects caused by any impurities that may be present in any composition derived from the production methods discussed above. One embodiment of a substantially pure virus particle is a cell lysate containing the virus particle that generates substantially no side effects when administered to an animal in an effective amount to deliver a nucleic acid sequence to desired cells in the animal. It is within the scope of the present invention to recover recombinant virus particles having a purity of up to and including about 99 percent.

One embodiment of the present invention is a gene delivery vehicle that is capable of transferring a heterologous nucleic acid sequence of the present invention into a host cell. The gene delivery vehicle includes a recombinant vector of the present invention, which preferably is encapsidated in a virus capsid to form a recombinant virus particle. Alternatively, the vector can be attached to a carrier, such as a virus or liposome. Preferably, the virus capsid, liposome, or other suitable carrier is designed so as to deliver the recombinant vector to a selected population of host cells.

According to one embodiment, the gene delivery vehicle of the present invention is capable of selectively expressing a coding region in a selected population of cells. Such selective expression is achieved by activation of a control element that is operatively linked to the coding region and that is selectively expressed in that cell population. The coding region can encode an RNA or protein capable of treating a host cell into which the vehicle is introduced. For example, the coding region may encode an RNA or protein capable of restoring the function of a defective gene in the host cell. Alternatively, the coding region may encode an RNA or protein that can protect the host cell from disease, infection, or other harm. The selected population of cells can range from a single cell type to every cell in an animal, depending on the application.

A preferred gene delivery vehicle of the present invention is one that is capable of substantially destroying a selected population of host cells such as cancer cells, or cells infected with an infectious agent such as a virus, bacterium, or parasite. Such a gene delivery vehicle includes a heterologous response element selectively expressed by the particular targeted cell population operatively linked to a promoter and to a coding region. In one embodiment, the coding region encodes a compound that is substantially cytotoxic to the cell population, such as a diphtheria toxin or parvovirus NS1 protein.

One embodiment of the present invention is directed to a method to selectively deliver, or transfer, certain nucleic acid sequences to particular cell types and to selectively express such sequences in such cell types using gene delivery vehicles of the present invention. Preferred gene delivery vehicles are capable of delivering a recombinant vector to a target cell, the vector being capable of crossing the nuclear membrane into the nucleus, and replicating at least to form a double-stranded replicative form corresponding to the recombinant vector. The delivery vehicle of the present invention can include solely one or more recombinant vectors or can include one or more helper constructs as well. The recombinant vectors and helper constructs can be attached to a carrier, such as a virus or a liposome, or may be incorporated into one or more recombinant virus particles having capsids that are capable of targeting the delivery vehicle to selected cell types.

As heretofore disclosed, targeting of selected cell types can be accomplished by producing a virus particle having a capsid that targets the delivery vehicle to the desired cell types (i.e., a capsid that has a selective affinity toward particular cell types). Alternatively, carriers can be modified to target desired cell types by, for example, attaching monoclonal antibodies or other ligands to such carriers so as to achieve selective interaction with receptors or other molecules on the desired cell type.

Selective expression of nucleic acid sequences in certain cell types can also be accomplished by use of an appropriate control element, and particularly an appropriate response element. The targeting of gene delivery vehicles can also be improved by administering the vehicle at a site proximal to (i.e., near or at) the selected cell population. For example, a gene delivery vehicle of the present invention can be injected into the peritoneal cavity to treat ovarian cancer, injected into the brain to treat glioblastoma, or applied topically to treat a melanoma.

Gene delivery vehicles of the present invention are particularly useful for effecting transient gene therapy since preferred recombinant vectors of the present invention do not exhibit substantial integration into the host genome. As used herein, "transient gene therapy" refers to a therapy in which a gene is delivered to a cell where the gene's expression is maintained for a productive amount of time, but is not maintained permanently. As such, the delivery vehicles are particularly useful for treating temporal conditions, such as cancer, endometriosis, infection, fertility problems, and sex-related diseases, in which, for example, a gene encoding a cytotoxic agent is delivered to affected cells.

A preferred embodiment of the present invention is the use of gene delivery vehicles of the present invention to substantially destroy a selected population of cells in an animal, preferably a human, by administering to the animal at least one recombinant vector encoding at least one cytotoxic agent in an amount effective to substantially destroy, or kill, the selected population of cells. A recombinant vector that encodes a cytotoxic agent and that is capable of selectively killing a cell into which the vector is introduced is referred to as a cell-suicide vector. Autonomous parvoviruses are trophic for growing cells and, as such, can selectively express cytotoxic agents in growing cells but do not express substantial amounts of cytotoxic agents in non-growing cells. As such, autonomous parvovirus-based gene delivery vehicles are particularly advantageous for use in selectively destroying undesirable rapidly growing cells, such as cancer cells. Autonomous parvovirus cell-suicide vectors are likely to be safer than are cell-suicide vectors produced using viruses that also exhibit tropism for non-growing cells, such as adenoviruses which express genes in both growing and non-growing cells. The selectivity afforded by gene delivery vehicles of the present invention suggest that such vehicles will have significantly fewer and less severe side effects than cytotoxic treatments currently used such as chemotherapy.

Recombinant cell-suicide vectors are preferably encapsidated in virus particles that, based on their capsids, preferably target desired populations of cells. Operatively linking a nucleic acid sequence encoding a cytotoxic agent to a response element that is selectively activated in the desired population of cells provides yet another safeguard to the gene delivery vehicle (i.e., that the cytotoxic agent is unlikely to be expressed in cell types other than desired cell types).

Such gene delivery vehicles can be used to target a variety of conditions caused by, for example, endometriosis, cancer (e.g., ovarian cancer, brain cancer, cancers of the immune system, breast cancer, liver cancer) or infection by an infectious agent (e.g., hepatitis, herpes, AIDS, opportunistic diseases associated with HIV infection, such as tuberculosis, or infection by Pneumocystis or Cryptococcus. As demonstrated by the specific embodiments described herein and as supported by the Examples below, it is within the ordinary skill of a person in any of the above fields to design and implement various gene delivery vehicles given the teachings presented herein.

A specific embodiment demonstrating the use of a gene delivery vehicle of the present invention to selectively destroy cells includes the use of a recombinant LuIII parvovirus particle which contains a parvovirus NS gene and/or a diphtheria toxin gene under the control of a progesterone receptor response element to target and kill breast cancer cells. Another embodiment is the use of a recombinant feline panleukopenia virus particle or a recombinant MVMi particle which contains a parvovirus NS gene and/or diphtheria toxin gene under the control of an immunoglobulin enhancer (e.g., a heavy chain enhancer or a kappa light chain enhancer) to target and kill B-cell leukemias or lymphomas. Yet another embodiment is a recombinant LuIII autonomous virus particle which contains a diphtheria toxin gene under the control of a T cell-specific response element, such as an IL-2 or IL-2 receptor response element. Another embodiment is the use of a recombinant virus particle containing components of a hepatitis virus capsid capable of targeting liver cells and a recombinant vector containing a diphtheria toxin gene under the control of a hepatitis control element to target and kill hepatomas or hepatitis-infected cells.

It should also be appreciated that gene delivery vehicles of the present invention can be used to effect stable gene therapy if the recombinant vectors are genetically engineered to integrate into the host genome by, for example, homologous recombination. In accordance with this embodiment, functions destroyed by genetic defects can be restored, such as defective globin genes (e.g., in thalassemia) and defective LDL genes in familial hypercholesteremia.

Gene delivery vehicles of the present invention can be formulations administered to animals either in vivo or ex vivo using a protocol that effectively transfers, or delivers, heterologous nucleic acid sequences to targeted cells. An administration protocol would include individual dose size, number of doses, frequency of dose administration, and mode of administration. A suitable dose of a gene delivery vehicle is a dose that is capable of transferring a nucleic acid sequence to a desired cell population when administered one or more times over a suitable time period.

Gene delivery vehicles can be formulated for administration using techniques known to those skilled in the art depending on the nature of the vehicle and the mode of administration. For example, a recombinant virus particle can be formulated in a manner similar to a live virus vaccine, such as in an aqueous physiologically-balanced salt solution for injection, or in a buffered oral formulation that is tolerable to the animal.

Gene delivery vehicles of the present invention can be administered to any animal, with humans, cattle, pigs, dogs, and cats being preferred. Gene delivery vehicles can be administered ex vivo or in vivo, with in vivo administration being either systemic or proximal to the location of the targeted cell population (e.g., at or near a tumor site). Gene delivery vehicles can be administered in a variety of ways including, but not limited to, injection (e.g., intravenous, subcutaneous, intradermal, intramuscular, or intraperitoneal), oral application, nasal application, or topical application. According to one embodiment, a selected population of cells in an animal can be treated in vivo (i.e., a heterologous nucleic sequence can be transferred, or delivered, to the selected population of cells) by administering to the animal a dose of at least about 1 infectious unit of recombinant virus particle per targeted cell in the population. If a carrier other than a virus particle is used, an equivalent amount of recombinant vector is administered. A preferred method of administration is by injection. For example, an ovarian tumor having about $1 \times 10^9$ cells can be treated by injecting into the peritoneal cavity a gene delivery vehicle formulation comprising at least about $1 \times 10^9$ infectious units.

"Boosters" of a gene delivery vehicle formulation are preferably administered when the gene delivery vehicle is no longer functioning effectively.

Gene delivery vehicles administered ex vivo can be accomplished by removing a selected cell population (e.g., bone marrow cells) from the body of the animal to receive the vehicle, transfecting or infecting the removed cells with a gene delivery vehicle of the present invention, and re-introducing the transfected or infected cells to the animal.

Another aspect of the present invention is the use of recombinant autonomous parvovirus vectors to produce RNA or protein products in, for example, cell culture or a transgenic animal. In one embodiment, an autonomous parvovirus vector capable of self-amplification and containing a heterologous nucleic acid sequence that encodes a desired RNA or protein product, operatively linked to a control element, is transfected into a desired cell type. The transfected cell is cultured in an effective medium to produce the desired product, which is then recovered. As used herein, recovery simply refers to collecting the whole fermentation medium comprising the product, cells, and fermentation broth, and need not imply additional steps of separation or purification, although such steps may be desired. The product can be further separated and/or purified from the fermentation medium using a variety of techniques known in the art.

In another embodiment, an autonomous parvovirus vector that is essentially incapable of self-amplification is co-transfected into a desired cell type with a helper construct that is capable of effecting replication of the recombinant vector. In yet another embodiment, in which production is transient, replication functions are not required.

Recombinant autonomous parvovirus vectors can be used in the production of any desired RNA or protein product. One advantage in the use of vectors of the present invention is that such vectors require very few proteins in order to maintain themselves in transfected host cells. As such, a large percentage of the substrate and energy involved in the culturing step can be targeted to production of desired product.

The following experimental results are provided for purposes of illustration and are not intended to limit the scope of the invention.

EXAMPLES

Example 1

Recombinant Autonomous Parvovirus Vectors

This example describes the production of recombinant autonomous parvovirus vectors, pGLuLUC, pGLuLUCΔSV, pGLuLUCΔSVrep⁻, and pGLuZ, which contain heterologous coding regions operatively linked to one or more transcription control sequences. Except when specified, techniques for producing the vectors can be found in Sambrook et al., ibid.

A. pGLuLUC

Recombinant vector pGLuLUC, in which the firefly luciferase gene is operatively linked to LuIII P4 and SV40 early promoters (examples of transcription control sequences) and which contains the LuIII terminal repeats, was constructed from the LuIII parvovirus cDNA clone pGLu883 in the following manner. pGLu883, depicted in FIG. 1, is an infectious genomic clone of LuIII ligated to pUC19 (Diffoot et al., 1989, ibid.; depicted in FIG. 1) Vector pGLu883ΔXba, a vector which lacked the XbaI site in the pUC cloning vector but retained the two closely spaced XbaI sites of LuIII, was generated by partially digesting pGLu883 using XbaI restriction endonuclease, filling in the ends using Klenow DNA polymerase plus nucleoside triphosphates, applying the blunt-ended digest to electrophoresis in a low melting agarose gel, isolating the desired fragment from the gel, and self-ligating the fragment to form pGLu883ΔXba. pGLu883ΔXba was identified by its XbaI restriction digest pattern. pGLuLUC was then produced by digesting pGLu883ΔXba with NcoI and XbaI to obtain a NcoI/XbaI fragment lacking the entire coding sequence of LuIII except for a 27 nucleotide stretch immediately 3' of the XbaI site which corresponded to the C-terminus of the coat protein.

The ends of the NcoI/XbaI fragment were "blunted", using mung bean nuclease. The blunt-ended NcoI/XbaI fragment was ligated to a 2.2-kb blunt-ended BamH1/DraI fragment isolated from pSV2A.L-A.Δ5' (see de Wet et al., pp. 725–737, 1987, Mol. Cell. Biol., Vol. 7) containing an SV40 early promoter operatively linked to the firefly luciferase gene. The resulting vector, denoted pGLuLUC, is depicted in FIG. 1.

In all Figures depicting vectors and helper constructs, "P4", "P38", and "SV" indicate that transcription was initiated from, respectively, LuIII P4, LuIII P38, and SV40 early promoters; "TO", "PRE$_2$", and "MMTV" indicate, respectively, a tetracycline response element, a progesterone receptor response element, and a mouse mammary tumor virus long terminal repeat response element, each of which is linked to a minimal promoter; "NS" indicates the coding region for nonstructural polypeptides; "VP" or "VPs" each indicates the coding region for autonomous parvovirus structural polypeptides; solid black boxes indicate the terminal repeats, "L" indicating the left end repeat, and "R" indicating the right end repeat; "Δ" indicates deletions in the marked terminal repeat(s); "An" indicates the polyadenylation site; "X" indicates an XbaI restriction site; and "TAA" indicates a translation termination codon. The Figures show the autonomous parvovirus and heterologous nucleic acid sequence regions of the vectors, which in toto, are circular plasmids.

B. pGLuLUCΔSV

Recombinant vector pGLuLUCΔSV, which is similar to pGLuLUC but lacks the SV40 early promoter, was constructed by ligating the blunt-ended NcoI/XbaI fragment of pGLu883ΔXba described in Example 1A to a blunt-ended 1.9 kb HindIII/DraI fragment of pSV2A.L-A.Δ5' that contains the luciferase gene but lacks the SV40 early promoter. The resulting vector, denoted pGLuLUCΔSV and depicted in FIG. 1, contains the LuIII P4 promoter operatively linked to the luciferase gene and the LuIII terminal repeats.

C. pGLuLUCΔSVrep⁻ pGLuLUCΔSVrep⁻, a control vector similar to pGLuLUCΔSV but lacking substantial portions of the LuIII terminal repeats (i.e., lacking cis-acting control elements), was produced by ligating the 1.9 kb blunt-ended HindIII/DraI fragment of pSV2A.L-A.Δ5' described in Example 1B to a blunt-ended NcoI/XbaI fragment of pGLuΔBE (Hanson and Rhode, pp. 4325–4333, 1991, J. Virology, Vol. 65; see also Example 2) that contains the P4 promoter and portions of the terminal repeats. The resulting control vector, denoted pGLuLUCΔSVrep⁻, contains the LuIII P4 promoter operatively linked to the luciferase gene, but lacks at least some of the cis-acting elements normally found in the LuIII terminal repeats. The vector is depicted in FIG. 1.

D. pGLuZ

Recombinant vector pGLuZ, which contains a β-galactosidase gene operatively linked to a LuIII P4 promoter and the LuIII terminal repeats, was made by ligating the blunt-ended NcoI/XbaI fragment of pGLu883ΔXba described in Example 1A to a blunt-ended restriction fragment of placD (obtained from Dr. Richard D. Palmiter, University of Washington, Seattle, Wash.) containing the Escherichia coli β-galactosidase gene. The resulting vector, denoted pGLuZ, is depicted in FIG. 1.

Example 2

Autonomous Parvovirus Helper Constructs

This example describes the production of autonomous parvovirus helper constructs pGLuΔBE and pSVLu.

A. pGLuΔBE

Helper construct pGLuΔBE, which is similar to the LuIII genome except that it lacks a substantially portion of the terminal repeats, was generated from pGLu883 as described by Hanson and Rhode, ibid. The resulting helper construct, denoted pGLuΔBE and depicted in FIG. 1, contains the LuIII P4 promoter operatively linked to the LuIII NS gene and the LuIII P38 promoter operatively linked to the LuIII VP gene, but lacking a substantial portion of the LuIII terminal repeat sequences. As such, pGLuΔBE can provide both nonstructural and structural LuIII polypeptides in trans.

B. pSVLu pSVLu, which lacks the LuIII terminal repeats and in which NS gene expression is operatively linked to an SV40 early promoter was constructed by ligating a 4.5-kb BamHI/SalI fragment of pP38Lu2ΔNd2 (see Rhode, pp. 4249–4256, 1989, *J. Virology*, Vol. 63) that contains the LuIII NS coding region as well as the VP coding region operatively linked to the P38 promoter between the BglII and SalI sites of pECE (see Ellis et al., pp. 721–732, 1986, *Cell*, Vol 45) such that the NS coding region is operatively linked to the SV40 promoter of pECE. The resulting vector, denoted pSVLu and depicted in FIG. 1, can provide both nonstructural and structural LuIII polypeptides in trans.

Example 3

Expression of Genes Transferred into Cells using Recombinant Vectors and Helper Constructs This example describes the transfer and expression of heterologous nucleic acid sequences in HeLa cells.

Recombinant vectors and helper constructs were transfected into HeLa cells by electroporation as described by Maxwell et al., pp. 557–562, 1988, DNA, Vol. 7, using a Bio-Rad Gene Pulser (available from Bio-Rad Laboratories, Hercules, Calif.) or an IBI Gene Zapper (available from International Biotechnologies, New Haven, Conn.). The capacitance settings were adjusted according to the volume of cell suspension to be pulsed so as to maintain a time constant of approximately 30 milliseconds. Voltages used were 0.21 kv for HeLa cells and for 293 cells and 0.23 kv for NB324K cells.

Transfer of the luciferase gene to HeLa cells using autonomous parvovirus vectors was accomplished in the following manner. HeLa cells, at a concentration of about 0.7 to 1.0×10$^7$ cells per ml in electroporation buffer (see Maxwell et al., 1988, ibid.), were electroporated with either 25 micrograms (μg) per ml or 50 μg per ml of vectors pGLuLUC, pGLuLUCΔSV, or pGLuLUCΔSVrep$^-$, with or without 10 μg per ml of the helper construct pGLuΔBE. The electroporated cells were cultured overnight in OptiMEM medium (GIBCO, Gaithersburg, Md.) containing 10% fetal bovine serum. The serum was then changed to OptiMEM containing 3.8% fetal bovine serum and the cells incubated for an additional about 28 hours. Cell extracts were prepared and assayed for luciferase activity as described previously (Maxwell et al., 1988, ibid.) using a Monolight 2001 luminometer (Analytical Luminescence Laboratory, San Diego, Calif.). The results are shown in Table 1.

TABLE 1

EXPRESSION OF LUCIFERASE IN TRANSIENT TRANSFECTIONS OF HeLa CELLS USING LuIII RECOMBINANT VECTORS, WITH OR WITHOUT HELPER CONSTRUCTS

| Recombinant plasmid | LU$^a$/100 μg protein | | Fold activation by helper |
|---|---|---|---|
| | −Helper | +Helper | |
| Experiment 1 | | | |
| pGLuLUC | 9.68 × 10$^3$ | 4.24 × 10$^6$ | 438 |
| pGLuLUCΔSV | 8.15 × 10$^3$ | 4.69 × 10$^7$ | 5,760 |
| pGLuLUCΔSVrep$^-$ | 1.14 × 10$^4$ | 3.87 × 10$^5$ | 34 |
| Experiment 2 | | | |
| pGLuLUCΔSV | 2.0 × 10$^4$ | 8.18 × 10$^7$ | 4,100 |
| pGLuLUCΔSVrep$^-$ | 3.32 × 10$^4$ | 3.51 × 10$^6$ | 106 |

$^a$LU: arbitrary light units

Experiment 1 represents single electroporations while Experiment 2 represents means of duplicate electroporations. The results indicate that the expression of luciferase activity in HeLa cells co-transfected by recombinant virus vector pGLuLUC, pGLuLUCΔSV, or pGLuLUCΔSVrep− with the helper construct was significantly greater (see "fold activation by helper" column) than luciferase expression in cells transfected by the recombinant vector alone, ranging from about 30 to about 100-fold for pGLuLUCΔSVrep$^-$, about 400-fold for pGLuLUC, and greater than about 4000-fold for pGLuLUCΔSV. The results show that helper constructs of the present invention effect replication of recombinant vectors of the present invention.

Hirt extracts (see Hirt, pp. 365–369, 1967, *J. Mol. Biol.*, Vol. 26) were prepared from parallel samples of the transfected HeLa cells described above about 72 hours after transfection. Residual extra-cellular DNA from the transfection procedure was digested with DNase (at about 100–200 μg per ml) for several hours at about 37° C. Low molecular weight DNA was extracted from the transfected cells according to Hirt except using high speed centrifugation (about 40,000× g for 1 hour) of the high salt extracts. The nucleic acids obtained from the extraction were treated with RNase (about 250 μg per ml) for about 30 minutes at room temperature. Subsequently, about 50 percent of each sample was digested with DpnI. The resulting DNA samples were applied to agarose gel electrophoresis and transferred to a nylon membrane by the Southern blotting technique (see Sambrook et al, ibid.). The resulting DNA-containing membrane was hybridized with a digoxigenin-labeled luciferase DNA probe (i.e., the HindIII/DraI fragment isolated from pSV2A.L-A.Δ5') in a hybridization buffer of 7% sodium dodecyl sulfate, 0.5M phosphate (pH 6.8), 1 millimolar (mM) EDTA overnight at about 64° C. The membrane was washed according to standard methods. Synthesis and immunological detection of the hybridized probe were performed according to manufacturer's protocols (Genius™, Boehringer Mannheim, Indianapolis, Ind.).

The results indicate that excision and replication of recombinant LuIII genomic replicative form (RF) DNA was readily detected as monomeric (about 2.6 kb) and oligomeric forms in the cellular extracts of cells co-transfected with pGLuLUCΔSV and pGLuΔBE. RF production was also detected in cellular extracts from cells co-transfected with pGLuLUC and pGLuΔBE but the level was about one third less than that detected in cells co-transfected by pGLuLUCΔSV and pGLuΔBE. Essentially no RF production was detected in cellular extracts of cells co-transfected with pGLuLUCΔSVrep$^-$ and pGLuΔBE or in cells transfected with recombinant vector alone (i.e., without the pGLuΔBE helper construct).

Example 4

Production and use of Autonomous Parvovirus Infectious Particles to Transfer Genes This example describes the production of recombinant autonomous parvovirus particles and their use to transfer genes to a variety of mammalian cells, including Hela cells, 293 cells (human fetal kidney cells transformed by the E1 region of adenovirus), and NB324K cells (an SV40-transformed human cell line).

HeLa, 293, and NB324K cells were co-transfected with recombinant vector pGLuLUC, pGLuLUCΔSV, or pGLuLUCΔSVrep−, and helper construct pGLuΔBE and incubated as described in Example 3. Medium containing the released virus particles was collected at pre-determined times following electroporation and either centrifuged at low speed or filtered using an 0.2 micron filter to remove contaminants. The supernatants containing recombinant virus particles LuIII:pGLuLUC, LuIII:pGLuLUCΔSV, or LuIII:pGLuLUCΔSVrep− were collected and stored at about −20° C.

In order to test the infectivity of the recombinant virus particles, about 1 ml of each particle containing-supernatant was mixed with approximately $2 \times 10^5$ HeLa cells or 293 cells which had been cultured in a 6 cm dish in OptiMEM supplemented with 3.8% fetal bovine serum for one day at 37° C. Following incubation of the infected cells for 3 to 5 hours at 37° C., about 1.5 ml of fresh culture medium was added. The HeLa and 293 cells were cultured for increasing lengths of time and then tested for luciferase activity.

The results indicate that luciferase expression occurred in HeLa or 293 cells infected with either LuIII:pGLuLUC-containing or LuIII:pGLuLUCΔSV-containing supernatants, but not in cells infected with LuIII:pGLuLUCΔSVrep−-containing supernatants. Transducing activity of the virus particles produced by HeLa cells, as measured by luciferase activity, was detected for at least 7 days post infection, with a peak of activity from about 2 to 3 days post infection. Transducing activity of the virus particles produced by 293 cells increased for 3 to 4 days following transfection. It was also found that the transducing activity produced by transfected NB324K cells was higher than that produced by the transfected 293 cells. Experiments have also been conducted that show that transducing activity produced by transfected COS cells is comparable to that produced by transfected NB324K cells.

These results indicate the ability to produce recombinant virus particles of the present invention and their effective use as gene delivery vehicles.

Example 5

Transfer of β-Galactosidase Gene to NB324K Cells

This example describes the use of the recombinant vector pGLuZ to transfer and express the β-galactosidase gene in NB324K cells.

Recombinant vector pGLuZ and helper construct pSVLu were co-transfected into NB324K cells using the method described in Example 3 in order to produce LuIII:pGLuZ virus particles. Culture medium containing LuIII:pGLuZ virus particles was collected 3 days after transfection. NB324K and HeLa cells were infected with LuIII:pGLuZ virus particles in a manner similar to that described in Example 4 and cultured for 48 hours. The infected cells were then fixed and stained with X-gal (5-bromo-4-chloro-3-indolyl-β-D-galactopyranoside). Microscopy analysis of the stained cells indicates that the infected cells expressed β-galactosidase efficiently, indicating efficient transfer of nucleic acid sequences using gene delivery vehicles of the present invention.

Example 6

Infection of T47D Breast Cancer Cells

This example demonstrates that LuIII recombinant virus particles can infect human T47D breast cancer cells.

Replicate plates containing about $2 \times 10^5$ T47D breast cancer cells were infected with about 0.1 ml or 0.3 ml of LuIII:pGLuLUCΔSV virus particle-containing supernatant (diluted to 1 ml with medium) collected from NB324K cells as described in Example 3. Luciferase activity in the infected cells was measured 1 or 2 days following infection using the method described in Example 3. It was found that luciferase activity increased about 2-fold between day 1 and day 2. The luciferase activity in cells infected with 0.3 ml virus-containing medium was about 2-fold higher than in cells infected with 0.1 ml medium. Thus, LuIII recombinant virus vectors of the present invention are capable of infecting human breast cancer cells and transferring heterologous nucleic acids to such cells.

Example 7

Production and Use of Recombinant Vector pTOLuLUC and Recombinant Virus Particle LuIII:pTOLuLUC This example describes the construction of pTOLuLUC, a LuIII vector containing a heterologous control element (i.e., a tetracycline response element) and heterologous coding region (i.e., a luciferase gene), and its use as a gene delivery vehicle. The example describes production of LuIII:pTOLuLUC virus particles, infection of HtTA1 cells with such particles, and expression of luciferase in infected cells cultured in an effective media containing a wide range of tetracycline concentrations.

HtTA1 cells are HeLa cells that have been co-transfected with a vector containing the neo gene encoding neomycin resistance and plasmid pUHD15-1, an expression vector containing a cytomegalovirus (CMV) early promoter operatively linked to the tTA gene, which encodes tTA, a tetracycline repressor/herpes simplex virus C-terminal VP16 trans-activator protein (Gossen et al., pp. 5547–5551, 1992, Proc. Natl. Acad. Sci., Vol. 89). tTA is capable of trans-activating nucleic acid sequences operatively linked to a tetracycline response element comprising one or more copies of the tetracycline operator. The present Example uses TO, a tetracycline response element containing 7 copies of the tetracycline operator. See schematic drawing in FIG. 2A. As tetracycline is added to the medium, trans-activation decreases as a function of the tetracycline concentration over several orders of magnitude (Grossen et al., ibid.). As such, this system is very useful in studying how a protein functions as its concentration in the cell is varied.

Figure 2:
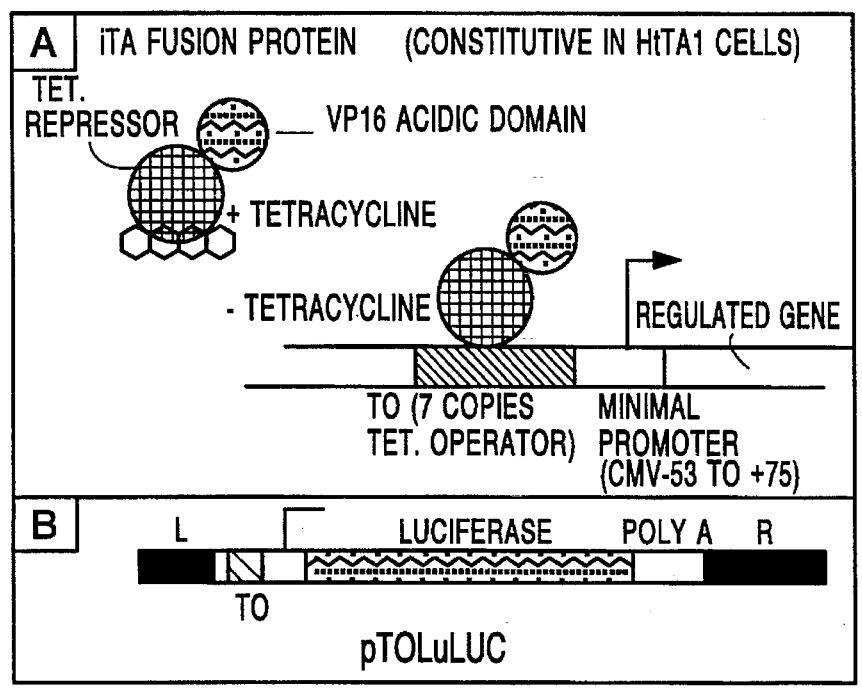
FIG. 2A–2C includes a schematic drawing depicting a portion of recombinant LuIII vector pTOLuLUC and a graph depicting the sensitivity of luciferase expression to tetracycline in HtTA1 cells infected with LuIII:pTOLuLUC.
Figure 2:
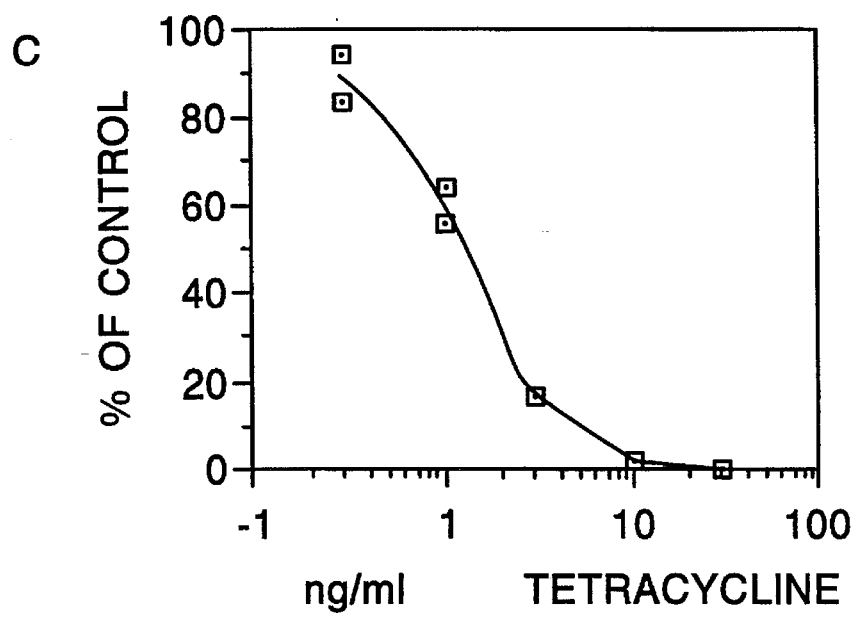

Referring to FIG. 2B, recombinant vector pTOLuLUC was produced by replacing the LuIII P4 promoter and coding regions of pGLu883 with a nucleic acid sequence containing a TO response element and a minimal, enhancerless CMV promoter operatively linked to the luciferase gene; LuIII terminal repeats were retained in the vector. Specifically, the luciferase gene with an upstream cloning array was ligated in place of LuIII coding sequences between the StyI site at about nucleotide 145 and the SspI site at about nucleotide 4677 of the LuIII genome. A BamHI fragment containing the TO response element and CMV promoter was converted into a BglII fragment and inserted into the BglII site of the cloning array upstream of the luciferase gene in the correct orientation.

Recombinant virus particle LuIII:pTOLuLUC was produced by co-transfection of pTOLuLUC and helper construct pSVLu into NB324K or COS cells using methods similar to those described in Example 3.

HtTA1 cells were infected with LuIII:pTOLuLUC virus particles and cultured as described in Example 4 in the presence of a variety of concentrations of tetracycline, as shown in FIG. 2C. The luciferase activity in the infected cell samples was measured about 30 hours after infection. The transferred luciferase gene was efficiently expressed when tetracycline was absent (about 130,000 luciferase units [LU]). A gradual decrease in luciferase activity was seen as the tetracycline concentration was increased from about 0.3 to 10 ng per ml. Infection of LuIII:pTOLuLUC into HeLa cells not expressing the tTA trans-activator gave barely detectable levels of luciferase, regardless of whether tetracycline was absent or present in the medium. Thus, heterologous response elements operatively linked to heterologous coding regions can be transferred to and properly expressed in desired cell types by gene delivery vehicles of the present invention.

Example 8

Gene Transfer of Toxin Genes into Cancer Cells

This example demonstrates the ability to transfer a coding region encoding a cytotoxic agent to a cancer cell and to induce killing of the cancer cell. The toxin gene is operatively linked to a heterologous response element that is selectively trans-activated in the cancer cell.

Specifically, the example describes the construction of a LuIII recombinant vector containing a progesterone receptor (PRE) response element and a promoter operatively linked to a diphtheria toxin gene, recombinant virus particles containing that vector, infection of breast cancer cells with such particles, and the ability to kill breast cancer cells in the presence of progestin. The PRE response element was selected because of the abundance of progesterone receptors in certain breast cancer cells.

Recombinant vector pPRELuDT-A is produced by replacing the LuIII P4 promoter and coding regions of genomic clone pGLu883 with a nucleic acid sequence containing a PRE response element and a minimal, enhancerless CMV promoter operatively linked to a gene encoding the diphtheria toxin A chain; LuIII terminal repeats are retained in the vector. The PRE response element comprises two copies of an oligonucleotide representing the PRE consensus sequence (see Lieberman et al., 1993, Mol. Endocrin., in press).

Recombinant virus particle LuIII:pPRELuDT-A is produced by co-transfection of recombinant vector pPRE-LuDT-A and helper construct pSVLu into NB324K cells using methods similar to those described in Example 3.

Human breast cancer T47D cells are infected with LuII-I:pPRELuDT-A virus particles and cultured as described in Example 4 in the presence of the progesterone analog progestin R5020 at concentrations ranging from about $3 \times 10^{-11}$ to about $1 \times 10^{-9}$ moles/liter (M). The infected T47D cells are characterized for protein expression and cytotoxicity as a function of exposure to varying concentrations of progestin.

Example 9

Figure 3:
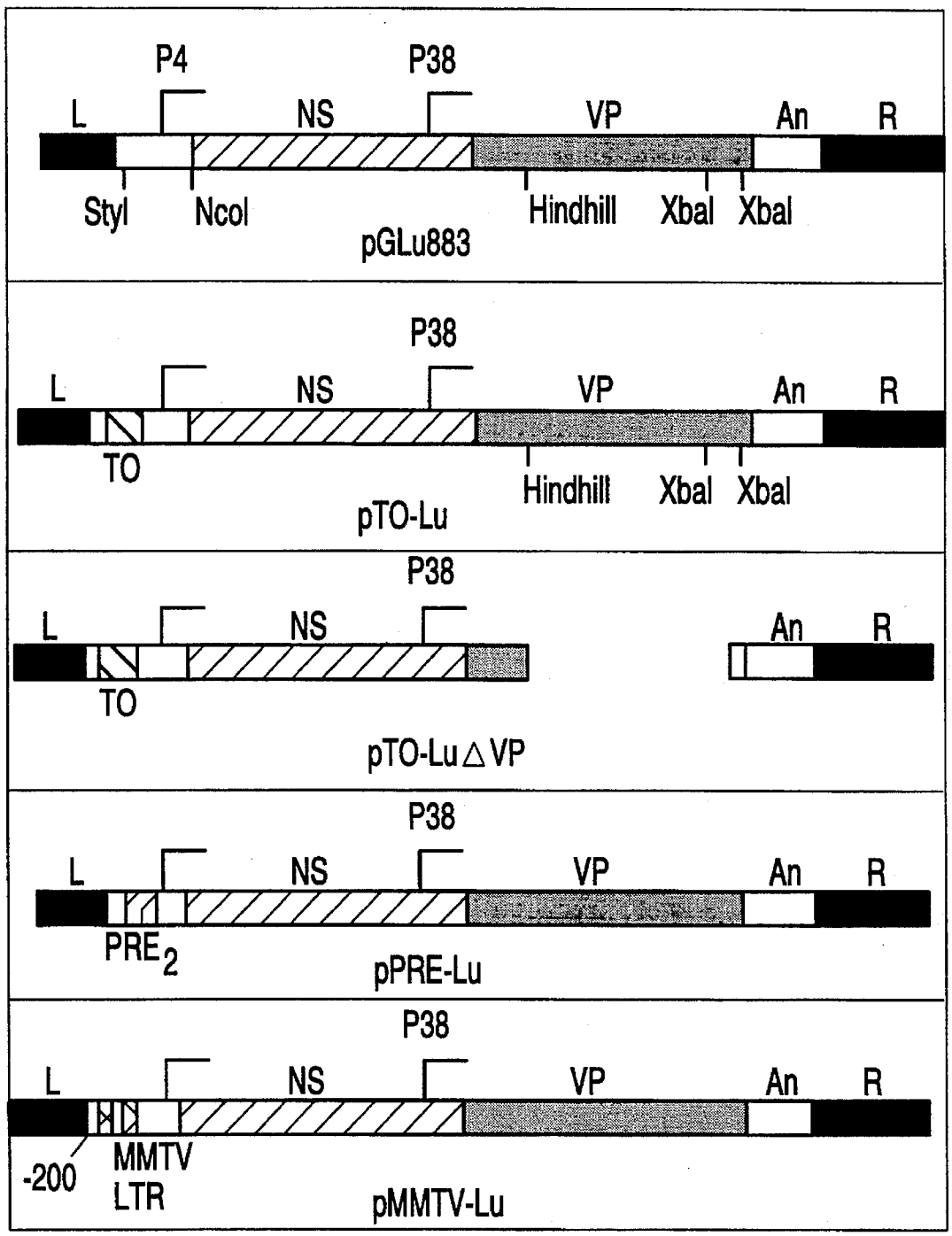
FIG. 3 includes schematic drawings depicting portions of additional recombinant autonomous parvovirus vectors of the present invention.
Figure 4:
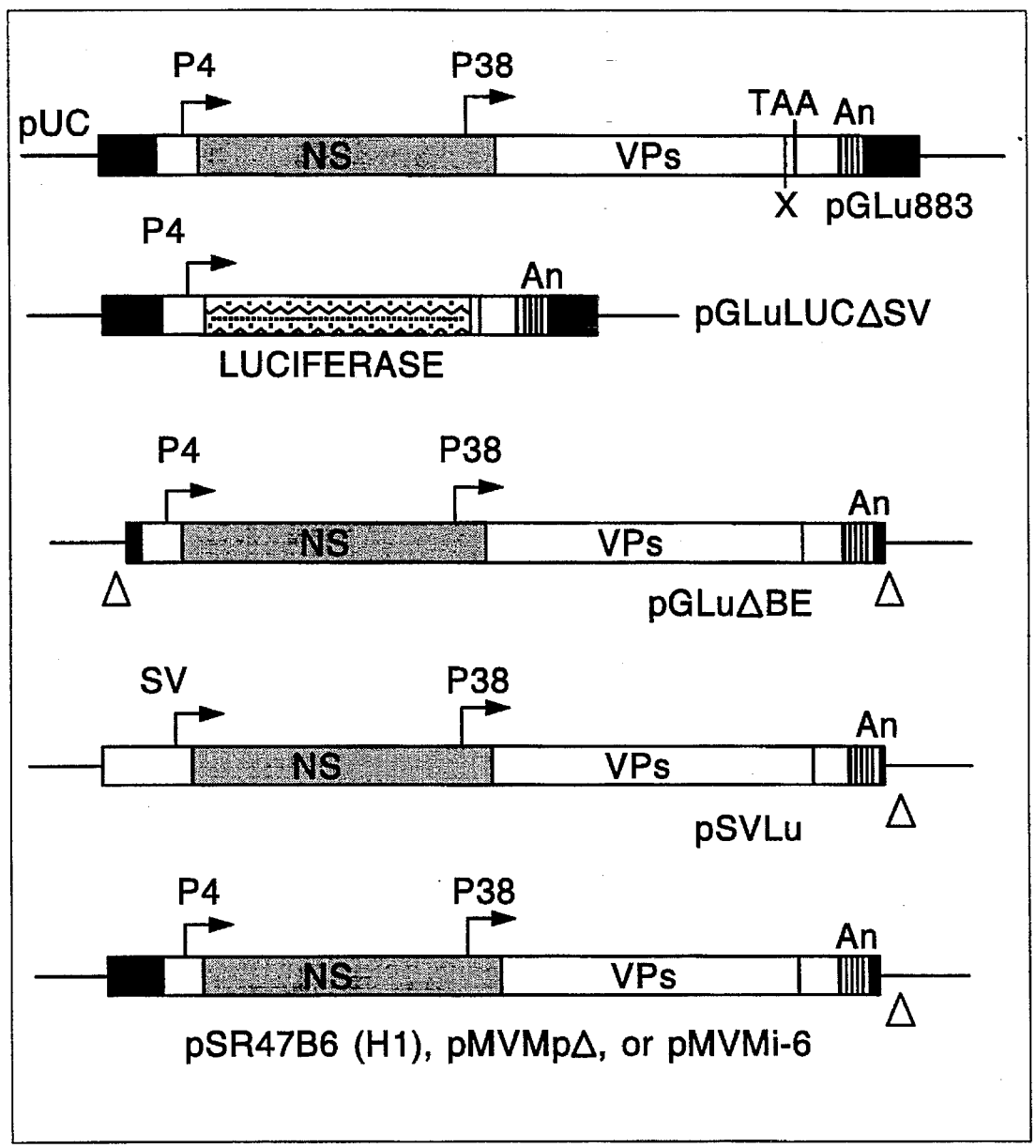
FIG. 4 includes schematic drawings depicting helper constructs capable of pseudotyping recombinant autonomous parvovirus vectors of the present invention.

Construction of Recombinant Vectors with the NS Gene Operatively Linked to a Heterologous Response Element and Use to Kill Cells This example describes production of several recombinant LuIII vectors in which expression of the LuIII NS gene is under the control of a tetracycline (TO) response element, a progesterone receptor (PRE) response element, a mouse mammary tumor virus (MMTV) response element, or a LuIII P38 promoter. The example also describes recombinant virus particles containing such vectors and their use as gene delivery vehicles. Such vectors can also be used to study the function of NS1 protein.

pTO-Lu pTO-Lu, depicted in FIG. 3, is produced by replacing the P4 promoter region of the LuIII infectious clone pGLu883 with a TO response element and minimal promoter (including a TATA box and transcription initiation site). Specifically, pGLu883 is partially digested with StyI and NcoI and the StyI/NcoI restriction fragment containing the P4 promoter replaced with an about 470 bp DNA fragment containing the TO response element and minimal enhancerless CMV promoter, similar to that used in construction of pTOLuLUC in Example 7.

Recombinant virus particle LuIII:pTO-Lu is produced by co-transfecting NB324K cells with vector pTO-Lu and helper construct pSVLu according to the method described in Example 4. The resulting LuIII:pTO-Lu virus particles are used to infect HtTA1 cells and/or 324K-tTA cells as described in Example 4. 324K-tTA cells are an NB324K cell line transfected with the tTA gene in a manner analogous to the method by which HtTA1 was produced. The infected cells are subsequently cultured in the absence or presence of varying concentrations of tetracycline to obtain cells having varying amounts of NS1 protein. The cells are analyzed for NS1 concentration and cytotoxicity.

B. pTO-LuΔVP pTO-LuΔVP, depicted in FIG. 3, is similar to pTO-Lu except that pTO-LuΔVP lacks the majority of the LuIII VP coding region, due to removal of an about 1.9-kb fragment from that coding region. As such, pTO-LuΔVP can be used to study NS1 function without the potential interference of virus assembly.

Recombinant virus particle LuIII:pTO-LuΔVP is produced by co-transfecting NB324K cells with vector pTO-LuΔVP and helper construct pSVLu. HtTA1 and 324K-tTA cells are infected with LuIII:pTO-LuΔVP virus and cultured in the presence of varying concentrations of tetracycline as described in Example 7. The cells are examined for NS1 production and cytotoxic following infection.

C. pPRE-Lu and pMMTV-Lu

Recombinant vectors pPRE-Lu and pMMTV-Lu, depicted in FIG. 3, are recombinant LuIII vectors in which expression of the NS gene is controlled by a PRE or MMTV response element, respectively. Expression of the NS gene operatively linked to the PRE response element is responsive to progesterone, whereas expression of NS operatively linked to the MMTV response element is responsive to progesterone as well as glucocorticoids.

Recombinant vector pPRE-Lu is produced by replacing the P4 promoter region of the LuIII infectious clone pGLu883 with two copies of the PRE consensus sequence combined with a minimal promoter such as the TATA box plus cap site, as in Example 8. Recombinant vector pMMTV-Lu is produced by replacing the P4 promoter region of pGLu883 with a control element spanning from about −200 to about +20 (assuming the transcription initiation site is at +1) of the MMTV genome.

Recombinant virus particles LuIII:pPRE-Lu and LuII-I:pMMTV-Lu are produced by co-transfecting NB324K cells with the respective vector and helper construct pSVLu by a method similar to that described in Example 4. The virus particles are then used to transfer the recombinant vectors to breast cancer cells where the expression of the NS gene can be studied, particularly in response to progesterone stimulation.

D. Cytotoxic Activity of the NS Gene

This Example describes methods to study the cytotoxic activity of the NS gene using recombinant vectors and virus particles of the present invention.

HtTA1 and 324K-tTA cells are infected with LuIII:pTO-LuΔVP virus in the presence of varying concentrations of tetracycline such as 0, 0.1, 1.0, and 10 ng of tetracycline per ml of medium. The infected cells are examined at about 24 to about 48 hours after infection for production and intracellular location of NS1 by enzyme linked immunoassay (ELISA) and immunofluorescence microscopy using polyclonal antibodies raised against a conserved region of MVM NS1 fusion protein or against peptides specific for LuIII NS1 and NS2.

Cell viability and NS1 protein production are correlated in infected cells by isolating cell samples at about 12 to 24 hour intervals for up to about 6 days after infection of HtTA1 and 324K-tTA cells with the LuIII:pTO-LuΔVP virus particle. Cell viability is determined using Trypan blue exclusion and/or MTT assays (Promega Corp., Madison, Wis.). Levels of NS1 and NS2 proteins are determined by submitting cell extracts produced from cell samples collected at the same time points as the cell viability samples to SDS gel electrophoresis and Western blotting using the polyclonal antibodies described above. The rate of synthesis of NS1 is determined at varying time points by pulse labeling infected cells with $^{35}$S-methionine, immunoprecipitating NS1 protein from cell extracts and analyzing by SDS gel electrophoresis.

Exponentially growing T47D breast cancer cells are infected with LuIII:pPRE-Lu virus in the presence of about $3\times10^{-11}$ to about $3\times10^{-9}$ M progestin R5020. The production of LuIII NS proteins, in particular NS1 proteins, and cell survival is monitored over a period of several days by assaying for the presence of NS proteins using the polyclonal antibodies described above. To achieve preferential killing of tumor cells, progestin R5020 is removed and replenished periodically to sustain high levels of NS1 expression in cells infected with virus particle LuIII:pPRE-Lu.

Example 10

Pseudotyping of Recombinant LuIII Vectors

This example demonstrates the ability to encapsidate recombinant LuIII vectors in MVMi, MVMp, and H1 parvovirus capsids, thereby permitting the transfer of nucleic acid sequences present on a LuIII vector to cells permissive for MVMi, MVMp, or H1 infection.

A. Construction of helper constructs

The replication defective autonomous parvovirus helper construct pSR47B6 was produced by deleting the right inverted repeat of wild-type hamster parvovirus H1; see Rhode, pp. 886–889, 1985, *J. Virology*, Vol. 55.

Helper construct pMVMpΔ, a replication defective form of the wild-type MVMp genome, was produced by deleting a substantial portion (about 90 nucleotides) of the right terminal repeat of the MVMp genome. The deletion was accomplished by transforming *Escherichia coli* HB101 with a plasmid containing an infectious MVMp genome and repeatedly subculturing the transformed strain for a week. Plasmids in which a substantial portion of the right terminal repeat was deleted were identified by SspI digestion.

Helper construct pMVMi-6, a replication defective form of the wild-type MVMi genome, was produced by deleting a substantial portion (about 170 nucleotides) of the right terminal repeat of the MVMi genome using the method by which pMVMpΔ was derived.

B. H1 Pseudotyping of LuIII Recombinant Vectors

Recombinant virus particles LuIII:pGLuLUCΔSV and H1:pGLuLUCΔSV were produced by co-transfecting both NB324K and PEJ/Rat2 cells (each at a concentration of about 0.7 to $1.0\times10^7$ cells per ml of electroporation buffer) with about 25 μg of pGLuLUCΔSV DNA per ml and with either pGLuΔBE or pSR47B6 helper constructs at concentrations of about 20, 30, or 40 μg of helper per ml according to the method described in Example 3. Virus particles LuIII:pGLuLUCΔSV and Hi:pGLuLUCΔSV produced by both NB324K and PEJ/Rat2 cells were collected from culture medium about 3 to 4 days after transfection as described in Example 3.

About $2\times10^5$ HeLa cells per 6 cm dish were infected with about 0.3 ml (diluted to 1 ml with medium) of supernatants containing LuIII:pGLuLUCΔSV or HI:pGLuLUCΔSV virus particles produced by NB324K or PEJ/Rat2 cells. Infected cells were incubated for about 4 hours at about 37° C., at which time about 1.5 ml of fresh medium was added to each dish, and the cells incubated for an additional about 20 to 29 hours. The cells were assayed for luciferase activity according to the method described above in Example 3.

The infection experiments indicated that both pGLuΔBE and pSR47B6 helper constructs were able to support virus production in both NB324K and PEJ/Rat2 cells. In particular, the results indicate that an H1 helper construct can promote both amplification and packaging of a recombinant LuIII vector resulting in functional recombinant virus particles having the LuIII vector encapsidated in an H1 capsid.

C. MVMp and MVMi Pseudotyping of LuIII Recombinant Vectors

Recombinant virus particles, LuIII:pGLuLUCΔSV, MVMi:pGLuLUCΔSV and MVMp:pGLuLUCΔSV were produced by co-transfecting NB324K cells (at a concentration of about 0.7 to $1.0\times10^7$ cells per ml of electroporation buffer) with about 25 μg of pGLuLUCΔSV DNA per ml and with about 40 μg of either pSVLu, pMVMi-6, or pMVMpΔ helper constructs per ml according to the method described in Example 3. Recombinant virus particles LuIII:pGLuLUCΔSV, MVMi:pGLuLUCΔSV and MVMp:pGLuLUCΔSV were collected from culture medium about 3 to 4 days after transfection as described in Example 3.

About $2\times10^5$ HeLa cells or NB324K cells per 6 cm dish were infected with about 0.3 ml (diluted to 1 ml with medium) of supernatants containing LuIII:pGLuLUCΔSV, MVMi:pGLuLUCΔSV and MVMp:pGLuLUCΔSV virus particles. Infected cells were incubated for about 4 hours at about 37° C., at which time about 1.5 ml of fresh medium was added to each dish, and the cells incubated for an additional about 20 to 29 hours. The cells were assayed for luciferase activity according to the method described above in Example 3.

The infection experiments indicated that pSVLu, pMVMi-6, and pMVMpΔ helper constructs were each able to support virus production in NB324K cells. In particular, the results indicate that a MVMi and MVMp helper constructs can promote both amplification and packaging of a recombinant LuIII vector resulting in functional recombinant virus particles having the LuIII vector encapsidated in either and MVMi or MVMp capsid.

D. Targeting of Pseudotyped Recombinant Virus Particles

This example shows that a recombinant LuIII vector encapsidated in an MVMi capsid displays a different host range than the same vector encapsidated in an MVMp capsid.

About $2 \times 10^5$ murine A9 fibroblast cells (permissive for wild-type MVMp but restrictive for wild-type MVMi infection; see Tattersall et al., pp. 944–955, 1983, *J. Virology*, Vol. 46) or murine iD5 cells (permissive for both wild-type MVMp and wild-type MVMi infection; see Ball-Goodrich et al., pp. 3415–3423, 1992, *J. Virology*, Vol. 66) were infected with about 0.3 ml (diluted to 1 ml with medium) of supernatants containing LuIII:pGLuLUCΔSV, MVMi:pGLuLUCΔSV and MVMp:pGLuLUCΔSV virus particles. Infected cells were incubated for about 4 hours at about 37° C., at which time about 1.5 ml of fresh medium was added to each dish, and the cells incubated for an additional about 20 to 29 hours. The cells were assayed for luciferase activity according to the method described above in Example 3.

The infection experiments demonstrated that fibroblast A9 cells exposed to MVMp:pGLuLUCΔSV virus particles produced greater than about 1400 times as much luciferase as did A9 cells exposed to MVMi:pGLuLUCΔSV virus particles. In contrast, iD5 cells exposed to either virus particle produced significant amounts of luciferase. Thus, the pseudotyped virus particles displayed the same host tropisms as do wild-type viruses having the same capsids. These results support the usefulness of pseudotyping in modifying the host range of a gene delivery vehicle of the present invention.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A recombinant vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

2. The vector of claim 1, wherein said heterologous nucleic acid sequence is selected from the group consisting of a heterologous control element and a heterologous coding region, said heterologous control element being operably linked to said heterologous coding region.

3. The vector of claim 1, wherein said heterologous control element comprises a heterologous response element.

4. The vector of claim 1, wherein said heterologous nucleic acid sequence comprises a heterologous control element operatively linked to a heterologous coding region.

5. The vector of claim 1, wherein said heterologous nucleic acid sequence comprises at least one heterologous response element operatively linked to a promoter selected from the group consisting of an autonomous parvovirus promoter and a heterologous promoter.

6. The vector of claim 2, wherein said heterologous control element is operatively linked to at least one coding region selected from the group consisting of an autonomous parvovirus coding region and said heterologous coding region.

7. The vector of claim 2, wherein said heterologous coding region is operatively linked to a transcription control sequence selected from the group consisting of an autonomous parvovirus transcription control sequence that regulates the expression of parvovirus nonstructural polypeptide genes, an autonomous parvovirus transcription control sequence that regulates the expression of parvovirus structural polypeptide genes, and a heterologous transcription control sequence comprising a promoter and at least one heterologous response element.

8. The vector of claim 1, wherein said vector is packaged into a virus particle.

9. The vector of claim 1, wherein said parvovirus nucleic acid sequences are selected from the group consisting of LuIII parvovirus, minute virus of mice, hamster parvovirus, feline panleukopenia virus, canine parvovirus, porcine parvovirus, latent rat virus, mink enteritis virus, human parvovirus, bovine parvovirus, and Aleutian mink disease parvovirus nucleic acid sequences.

10. The vector of claim 1, wherein said parvovirus nucleic acid sequences are selected from the group consisting of LuIII parvovirus, minute virus of mice MVMi, minute virus of mice MVMp, and hamster parvovirus Hi nucleic acid sequences.

11. The vector of claim 1, wherein said parvovirus nucleic acid sequences comprise a LuIII parvovirus nucleic acid sequence.

12. The vector of claim 2, wherein said heterologous coding region is operatively linked to an autonomous parvovirus P4 transcription control sequence.

13. The vector of claim 2, wherein said heterologous coding region is operatively linked to a LuIII P4 transcription control sequence.

14. The vector of claim 1, wherein said heterologous nucleic acid sequence is selected from the group consisting of a cell-selective response element, a hormone receptor response element, an antibiotic response element, and a carbohydrate response element.

15. The vector of claim 14, wherein said cell-selective response element is capable of being activated by a transactivating regulatory element selectively produced in a cell type to which said vector is targeted.

16. The vector of claim 15, wherein said cell type is selected from the group consisting of a cancer cell and a cell infected by an infectious agent.

17. The vector of claim 1, wherein said heterologous nucleic acid sequence is selected from the group consisting of a tetracycline response element, a GAL4 response element, a progesterone receptor response element, a glucocorticoid receptor response element, an immunoglobulin kappa light chain enhancer, an immunoglobulin heavy chain enhancer, an α-1-antitrypsin enhancer, a serum albumin enhancer, a chorionic gonadotropin α-chain enhancer, a chorionic gonadotropin β-chain enhancer, an IL-2 enhancer, an IL-2 receptor enhancer, and an HIV response element.

18. The vector of claim 1, wherein said heterologous nucleic acid sequence encodes a functional protein selected from the group consisting of a cytotoxic agent, an immunopotentiator, a vaccine antigen and functional equivalents thereof.

19. The vector of claim 1, wherein said heterologous nucleic acid sequence encodes a functional protein selected from the group consisting of a diphtheria toxin, a ricin toxin, a modeccin toxin, an abrin toxin, a Pseudomonas exotoxin, a shiga toxin, a pokeweed antiviral protein, α-amanitin, a ribosome inhibiting protein, an autonomous parvovirus nonstructural protein, HSV thymidine kinase, and functional equivalents thereof.

20. The vector of claim 1, wherein said heterologous nucleic acid sequence encodes a functional protein selected from the group consisting of a diphtheria A-chain toxin, an autonomous parvovirus NS1 protein, HSV thymidine kinase, and functional equivalents thereof.

21. The vector of claim 1, wherein said heterologous nucleic acid sequence encodes a functional RNA selected from the group consisting of an antisense RNA, a ribozyme, and an RNA-based drug.

22. The vector of claim 1, wherein said heterologous nucleic acid sequence encodes a marker protein.

23. The vector of claim 1, wherein said parvovirus nucleic acid sequences comprise the terminal repeats of said parvovirus and at least one transcription control sequence selected from the group consisting of a transcription control sequence that regulates the expression of autonomous parvovirus nonstructural polypeptide genes and a transcription control sequence that regulates the expression of autonomous parvovirus structural polypeptide genes.

24. The vector of claim 1, wherein said heterologous nucleic acid sequences replace autonomous parvovirus sequences from about nucleotide 265 to about nucleotide 4530, wherein said heterologous sequences share substantial homology with LuIII.

25. The vector of claim 1, wherein said heterologous nucleic acid sequences replace autonomous parvovirus sequences from about nucleotide 145 to about nucleotide 4677, wherein said heterologeous sequences share substantial homology with LuIII.

26. The vector of claim 1 wherein introduction of said vector into a host cell effects transient gene transfer of said heterologous coding region into said cell.

27. The vector of claim 2, wherein said heterologous control element comprises a cancer cell-selective response element, wherein said heterologous coding region encodes a cytotoxic agent, and wherein said vector upon introduction into a host cancer cell inhibits cancer cell growth.

28. The vector of claim 1, wherein said vector comprises a single stranded DNA molecule.

29. The vector of claim 1, wherein said vector comprises a double stranded DNA plasmid.

30. The vector of claim 1, wherein said vector is selected from the group consisting of pGLuLUCΔSV and pTOLuLUC.

31. The vector of claim 1, wherein said vector self-amplifies when provided with viral non-structural proteins by genetically-transformed host cell.

32. The vector of claim 1, wherein said vector is self-amplification incompetent.

33. The vector of claim 1, wherein said vector is self-packaging when provided with vector-packaging proteins by a genetically-transformed host cell.

34. The vector of claim 1, wherein said vector is self-packaging incompetent.

35. A recombinant virus particle comprising a recombinant vector packaged in an autonomous marvovirus capsid, said vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

36. A recombinant virus particle comprising a recombinant vector packaged in an autonomous parvovirus capsid, said vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said vector being in a non-integrating form within a cell after in vitro transfer of said vector.

37. The virus particle of claim 36, wherein said heterologous nucleic acid sequence is selected from the group consisting of a heterologous control element and a heterologous coding region.

38. The virus particle of claim 37, wherein said parvovirus nucleic acid sequences are selected from the group consisting of LuIII parvovirus, minute virus of mice, hamster parvovirus, feline panleukopenia virus, canine parvovirus, porcine parvovirus, latent rat virus, mink enteritis virus, human parvovirus, bovine parvovirus, and Aleutian mink disease parvovirus nucleic acid sequences.

39. The virus particle of claim 36, wherein said parvovirus nucleic acid sequences comprise a LuIII nucleic acid sequence.

40. The virus particle of claim 36, wherein said capsid is selected from the group consisting of LuIII parvovirus, minute virus of mice, hamster parvovirus, feline panleukopenia virus, canine parvovirus, porcine parvovirus, latent rat virus, mink enteritis virus, human parvovirus, bovine parvovirus, and Aleutian mink disease parvovirus nucleic acid sequences.

41. The virus particle of claim 36, wherein said capsid is selected from the group consisting of LuIII parvoVirus, minute virus of mice MVMi, minute virus of mice MVMp, and hamster parvovirus H1 capsids.

42. The virus particle of claim 36, wherein said capsid comprises a LuIII capsid.

43. The virus particle of claim 36, wherein said recombinant-vector is pseudotyped such that said vector is packaged in a capsid of a virus species other than the species of said parvovirus nucleic acid sequence.

44. The virus particle of claim 36, wherein said parvovirus nucleic acid sequences comprise a LuIII nucleic acid sequence and wherein said virus capsid is selected from the group consisting of LuIII parvovirus, minute virus of mice, hamster parvovirus, feline panleukopenia virus, canine parvovirus, porcine parvovirus, latent rat virus, and mink enteritis virus capsids.

45. The virus particle of claim 36, wherein said parvovirus nucleic acid sequences comprise a LuIII nucleic acid sequence and wherein said virus capsid is selected from the group consisting of LuIII parvovirus, minute virus of mice MVMi, minute virus of mice MVMp, and hamster parvovirus H1 capsids.

46. The virus particle of claim 36, wherein infection of said virus particle into a host cell effects transient gene transfer of said heterologous coding region into said cell.

47. The virus particle of claim 37, wherein said heterologous control element comprises a cancer cell-selective response element, wherein said heterologous coding region encodes a cytotoxic agent, and wherein infection of said virus particle into a host cancer cell inhibits cancer cell growth.

48. A gene delivery vehicle comprising a recombinant vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

49. The virus particle of claim 36, wherein said particle exhibits characteristics of an autonomous parvovirus, said characteristics comprising high stability, lack of integration, high titer, and maintenance of infectivity upon concentration.

50. A gene delivery vehicle comprising a recombinant vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeat, said vector being in a non-integrating form within a cell after in vitro transfer of said vector.

51. The gene delivery vehicle of claim 50, wherein said vector is packaged in an autonomous parvovirus capsid to form a recombinant virus particle effective to deliver said vector to said host cell.

52. The gene delivery vehicle of claim 51, wherein said capsid targets said virus particle to a selected population of host cells.

53. The gene delivery vehicle of claim 50, wherein said vector is attached to a carrier effective to deliver said vector to said host cell.

54. The gene delivery vehicle of claim 53, wherein said carrier is selected from the group consisting of liposomes and viruses.

55. The gene delivery vehicle of claim 52, wherein said heterologous nucleic acid sequence comprises a control element which is operably linked to a coding region, which control element is selectively functional in a particular population of cells and selectively directs expression of said coding region in said cell population.

56. The gene delivery vehicle of claim 50, wherein said heterologous nucleic acid sequence encodes an RNA or protein for treating said host cell.

57. The gene delivery vehicle of claim 50, wherein said vehicle upon introduction into said host cell is capable of substantially destroying a selected population of host cells, said heterologous nucleic acid sequence comprising a heterologous response element that is selectively expressed by said cell population, said response element being operatively linked to a promoter and to a coding region capable of encoding a compound that is substantially cytotoxic to said cell population.

58. The gene delivery vehicle of claim 57, wherein said compound is selected from the group consisting of a diphtheria toxin, an autonomous parvovirus NS1 protein, and HSV thymidine kinase.

59. A recombinant nucleic acid comprising nucleic acid sequences of an autonomous parvovirus joined to a heterologous nucleic acid sequence comprising a heterologous control element or heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said recombinant nucleic acid is in a non-integrating form when transferred into a cell.

60. The gene delivery vehicle of claim 50, wherein said heterologous nucleic acid sequence restores the function of a defective gene in said host cell.

61. A recombinant nucleic acid comprising nucleic acid sequences of an autonomous parvovirus joined to a heterologous nucleic acid sequence comprising a heterologous control element or heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said recombinant nucleic acid being in a non-integrating form within a cell after in vitro transfer of said recombinant nucleic acid.

62. The recombinant nucleic acid of claim 61, wherein said heterologous nucleic acid sequence comprises a heterologous control element operatively linked to a heterologous coding region.

63. The autonomous parvovirus helper construct pSVLu.

64. A non-integrating vector comprising nucleic acid sequences of an autonomous parvovirus joined to at least one heterologous nucleic acid sequence, the expression of which is regulated by a control element, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said autonomous parvovirus nucleic acid sequences being devoid of nucleic acid sequences encoding either structural or nonstructural autonomous parvovirus polypeptides.

65. The vector of claim 64, wherein said vector is packaged within an autonomous parvovirus capsid that target selected cell types.

66. The vector of claim 64, wherein said vector is capable of effecting transient expression of said heterologous nucleic acid sequence in a host cell.

67. A method for transferring a heterologous nucleic acid sequence into a host cell in vitro comprising introducing into said cell a recombinant vector comprising nucleic acid sequences of an autonomous parvovirus joined to at least one heterologous nucleic acid sequence selected from the group consisting of a heterologous control element and a heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

68. The vector of claim 67, wherein expression of said cytotoxic agent is sufficient to destroy selected cell types.

69. A method for transferring a heterologous nucleic acid sequence into a host cell in vitro comprising introducing into said cell a recombinant vector comprising nucleic acid sequences of an autonomous parvovirus joined to at least one heterologous nucleic acid sequence selected from the group consisting of a heterologous control element and a heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said vector being in a non-integrating form within a cell after in vitro transfer of said vector.

70. A method for transferring a heterologous nucleic acid sequence into a cell in vitro comprising infecting said cell with a recombinant virus particle comprising a recombinant vector packaged in an autonomous parvovirus capsid, said vector comprising nucleic acid sequences of an autonomous parvovirus joined to at least one heterologous nucleic acid sequence selected from the group consisting of a heterologous control element and a heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

71. A method for substantially destroying a selected population of cells comprising administering to an in vitro cell population at least one recombinant vector comprising autonomous parvovirus nucleic acid sequences joined to at least one heterologous nucleic acid sequence having a heterologous response element that is selectively functional in said cell population, said response element being operably linked to a promoter and to a coding region encoding a compound that is substantially cytotoxic to said cell population, said autonomous parvovirus nucleic acid sequences comprising functional left and right end inverted terminal repeats, said heterologous nucleic acid sequence being located between and operably linked to said nucleic acid sequences comprising said left and right inverted terminal repeats, wherein said vector is in a non-integrating form when transferred into a cell.

72. A method for transferring a heterologous nucleic acid sequence into a cell in vitro comprising infecting said cell with a recombinant virus particle comprising a recombinant vector packaged in an autonomous parvovirus capsid, said vector comprising nucleic acid sequences of an autonomous parvovirus joined to at least one heterologous nucleic acid sequence selected from the group consisting of a heterologous control element and a heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said vector being in a non-integrating form within a cell after in vitro transfer of said vector.

73. A method for substantially destroying a selected population of cells comprising administering to an in vitro cell population at least one recombinant vector comprising autonomous parvovirus nucleic acid sequences joined to at least one heterologous nucleic acid sequence having a heterologous response element that is selectively functional in said cell population, said response element being operably linked to a promoter and to a coding region encoding a compound that is substantially cytotoxic to said cell population, said autonomous parvovirus nucleic acid sequences comprising functional left and right end inverted terminal repeats, said heterologous nucleic acid sequence being located between and operably linked to said nucleic acid sequences comprising said left and right inverted terminal repeats, said vector being in a non-integrating form within a cell after in vitro transfer of said vector.

74. The method of claim 73, wherein said coding region encodes an antisense RNA, a ribozyme, an RNA-based drug, or a cytotoxic protein.

75. The method of claim 73, wherein said selected population of cells comprise cancer cells or cells infected with an infectious agent.

76. A method for producing a recombinant virus particle useful in the delivery of a gone to a targeted cell, comprising:
(a) co-transfecting a host cell in vitro with a recombinant non-integrating vector comprising acid sequences of an autonomous parvovirus joined to at least one heterologous nucleic acid sequence and with a helper construct that effects at least one function selected from the group consisting of amplification of said vector and packaging of said vector in a parvovirus capsid, said autonomous parvovirus nucleic acid sequences comprising functional left and right end inverted terminal repeats, said heterologous nucleic acid sequence being located between and operably linked to said nucleic acid sequences comprising said left and right inverted terminal repeats; and
(b) culturing said transfected host cell in an effective medium to produce a recombinant virus particle said vector being in a non-integrating form within a cell after in vitro transfer of said vector.

77. The method of claim 76 wherein said helper construct is pSVLu.

78. A method for producing a heterologous product selected from the group consisting of RNA products and protein products comprising:
(a) transfecting a host cell in vitro with a recombinant non-integrating vector comprising nucleic acid sequences of an autonomous parvovirus joined to at least one heterologous nucleic acid sequence encoding said product, said autonomous parvovirus nucleic acid sequences comprising functional left and right inverted terminal repeats, said heterologous nucleic acid sequence being located between and operably linked to said nucleic acid sequences comprising said left and right inverted terminal repeats; and
(b) culturing said transfected host cell in an effective medium to produce said product.

79. The method of claim 78, wherein said host cell is further transfected with a helper construct that effects replication of said vector.

80. A recombinant vector comprising nucleic acid sequences of an autonomous parvovirus joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats.

81. A recombinant virus particle comprising a recombinant vector packaged in an autonomous parvovirus capsid, said vector comprising autonomous parvovirus nucleic acid sequences joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats.

82. A gene delivery vehicle comprising a recombinant vector comprising autonomous parvovirus nucleic acid sequences joined to at least one heterologous nucleic acid sequence, said autonomous parvovirus nucleic acid sequences comprising functional left and right end inverted terminal repeats, said heterologous nucleic acid sequence being located between and operably linked to said nucleic acid sequences comprising said left and right inverted terminal repeats.

83. A recombinant nucleic acid comprising autonomous parvovirus nucleic acid sequences joined to a heterologous nucleic acid sequence comprising a heterologous control element or a heterologous coding region, said autonomous parvovirus nucleic acid sequences comprising functional left and right end inverted terminal repeats, said heterologous nucleic acid sequence being located between and operably linked to said nucleic acid sequences comprising said left and right inverted terminal repeats.

* * * * *